(12) United States Patent
Mortishire-Smith et al.

(10) Patent No.: US 12,014,803 B2
(45) Date of Patent: Jun. 18, 2024

(54) TECHNIQUES FOR SAMPLE ANALYSIS USING CONSENSUS LIBRARIES

(71) Applicant: Waters Technologies Ireland Limited, Dublin (IE)

(72) Inventors: Russell J. Mortishire-Smith, Macclesfield (GB); Johannes P. C. Vissers, Zevenbergen (NL)

(73) Assignee: Waters Technologies Ireland Limited, Dublin (IE)

( * ) Notice: Subject to any disclaimer, the term of this patent is extended or adjusted under 35 U.S.C. 154(b) by 716 days.

(21) Appl. No.: 15/733,972

(22) PCT Filed: May 31, 2019

(86) PCT No.: PCT/IB2019/054556
§ 371 (c)(1),
(2) Date: Dec. 1, 2020

(87) PCT Pub. No.: WO2019/229723
PCT Pub. Date: Dec. 5, 2019

(65) Prior Publication Data
US 2021/0217499 A1 Jul. 15, 2021

(30) Foreign Application Priority Data
Jun. 1, 2018 (GB) ...................... 1809041

(51) Int. Cl.
*G16C 20/20* (2019.01)
*G01N 27/623* (2021.01)
(Continued)

(52) U.S. Cl.
CPC ........... *G16C 20/20* (2019.02); *G01N 27/623* (2021.01); *G01N 30/7233* (2013.01);
(Continued)

(58) Field of Classification Search
CPC ........ G16C 20/20; G16C 20/90; G16C 60/00; G01N 27/623; G01N 30/7233;
(Continued)

(56) References Cited

U.S. PATENT DOCUMENTS

2005/0181973 A1  8/2005  Genove et al.

FOREIGN PATENT DOCUMENTS

| CN | 101971019 A | 2/2011 |
|---|---|---|
| WO | 2012099971 A2 | 7/2012 |

(Continued)

OTHER PUBLICATIONS

Olivon, et al ("Optimized experimental workflow for tandem mass spectrometry molecular networking in metabolomics," Analytical and Bioanalytical Chemistry, Springer, DE, vol. 409, No. 24, Jul. 31, 2017, pp. 5767-5778, XP036311919 (Year: 2017).*

(Continued)

*Primary Examiner* — Michael Maskell
(74) *Attorney, Agent, or Firm* — Goodwin Procter LLP

(57) ABSTRACT

Techniques and apparatus for generating consensus libraries for sample matrices (Flow A) and using the consensus libraries to determine unknown-unidentified components of a sample (Flow B) are described. For example, in an embodiment, an apparatus may include at least one memory, and processing circuitry (220) coupled to said at least one memory, wherein said processing circuitry is adapted to receive a plurality of sample matrix data sets (210a-210n) for a sample matrix generated via mass analysis of said sample matrix, and to generate a consensus library (220) for the sample matrix based on said plurality of sample matrix data sets, the consensus library comprising a plurality of known-unidentified components for the sample matrix.

20 Claims, 36 Drawing Sheets

(51) Int. Cl.
  *G01N 30/72* (2006.01)
  *G16C 20/90* (2019.01)
  *G16C 60/00* (2019.01)
  *G01N 30/86* (2006.01)

(52) U.S. Cl.
  CPC ............. *G16C 20/90* (2019.02); *G16C 60/00* (2019.02); *G01N 30/8686* (2013.01)

(58) Field of Classification Search
  CPC ....... G01N 30/8686; G01N 2030/8813; G01N 30/86; G01N 30/72; G01N 2030/8648
  USPC .................................................. 250/281, 282
  See application file for complete search history.

(56) References Cited

FOREIGN PATENT DOCUMENTS

WO      2016142692 A1    9/2016
WO      2017173390 A1    10/2017

OTHER PUBLICATIONS

Blazenovic, et al ("Software tools and approaches for compound identification of LC-MS/MS data in metabolomics" Metabolites, vol. 8, No. 2, May 2018, pp. 31-53 (Year: 2018).*

Olivon, F., et al., "Optimized experimental workflow for tandem mass spectrometry molecular networking in metabolomics", Analytical and Bioanalytical Chemistry, 409(24):5767-5778 (2017).

Lam, H., "Building and Searching Tandem Mass Spectral Libraries for Peptide Identification" Molecular and Cellular Proteomics 10(12) 10 pages (2011).

Blazenovic, I., et al., "Software Tools and Approaches for Compound Identification of LC-MS/MS Data in Metabolomics", Metabolites 8(31) 23 pages (2018).

Peisl, B.Y.L., et al., "Dark matter in host-microbiome metabolomics: Tackling the unknowns—A Review" Analytica Chimica ACTA 1037:13-27 (2018).

Little, J.L., et al., "Identification of Known Unknowns Utilizing Accurate Mass Data and Chemical Abstracts Service Databases", Journal of the American Society for Mass Spectrometry, 22(2):348-359 (2011).

International Search Report and Written Opinion for International application No. PCT/IB2019/054556, dated Oct. 17, 2019, 11 pages.

International Preliminary Report on Patentability for International Patent Application No. PCT/IB2019/054556, dated Dec. 10, 2020.

Preliminary Examination Report for United Kingdom Patent Application No. GB1809041.5, dated Apr. 11, 2019.

Search Report for United Kingdom Patent Application No. GB1809041.5, dated Sep. 10, 2019.

Examination Report for United Kingdom Patent Application No. GB1809041.5, dated May 31, 2022.

First Office Action for Chinese Patent Application No. 201980051309.4, dated Jul. 25, 2023.

Sun, C., et al., "Application of high performance liquid chromatography/mass spectrometry to rapid recognition of naturally occurring biologically active components", Scientia Sinica Chimica, 40(6):621-630, (2010).

* cited by examiner

| | A | B | C | D | E | F | G | H | I | J | K |
|---|---|---|---|---|---|---|---|---|---|---|---|
| 1 | Unknown | | | | | | | | | | |
| 2 | Unknown (0.01_195.0355m/z) | 154.0283 | 129.6 | 0.01 | 172.8616 | 128.8721 | 171.8485 | 171.8657 | 144.4684 | 174.8665 | 126.8 |
| 3 | Unknown (0.01_262.8572m/z) | 261.8500 | 140.1 | 0.01 | 172.8626 | 128.8721 | 144.8660 | 170.8672 | 218.8661 | 173.8685 | 229.1 |
| 4 | Unknown (0.01_272.8774m/z) | 271.8702 | 150.8 | 0.01 | 201.0464 | 144.8660 | 171.8649 | 244.7909 | 170.8672 | 202.0489 | 217.8 |
| 5 | Unknown (0.02_209.1895m/z) | 208.1823 | 162.3 | 0.02 | 201.0464 | 202.0436 | 171.0515 | 171.0343 | 201.8607 | 201.8094 | 172.0 |
| 6 | Unknown (0.02_609.2773m/z) | 608.2701 | 251.5 | 0.02 | 608.2750 | 607.2556 | 279.0923 | | | | |
| 7 | Unknown (0.03_214.8881m/z) | 213.4809 | 137.7 | 0.03 | 172.8621 | 128.8719 | 171.8686 | 202.8604 | 129.8797 | 127.8688 | 174.8 |
| 8 | Unknown (0.03_245.1098m/z) | 244.1026 | 150.4 | 0.03 | 201.0463 | 173.8656 | 170.8661 | 244.7911 | 173.0515 | 171.0348 | 127.8 |
| 9 | Unknown (0.03_258.8637m/z) | 257.8565 | 140.3 | 0.03 | 201.0463 | 172.8621 | 128.8719 | 144.8665 | 170.8661 | 171.0515 | 218.8 |
| 10 | Unknown (0.03_282.2197m/z) | 281.2125 | 177.3 | 0.03 | 172.8643 | | | | | | |
| 11 | Unknown (0.04_233.9039m/z) | 232.8967 | 147.7 | 0.04 | 172.8620 | 128.8717 | 170.8664 | 144.8666 | 129.8770 | 229.1398 | 173.8 |
| 12 | Unknown (0.04_236.1264m/z) | 235.1192 | 152.5 | 0.04 | 201.0462 | 173.0505 | 202.0489 | 218.8660 | 201.8616 | 171.0349 | 91.0 |
| 13 | Unknown (0.04_411.2413m/z) | 410.2341 | 218.6 | 0.04 | 311.1647 | 309.1548 | 128.8790 | 312.1738 | | | |
| 14 | Unknown (0.05_137.9642m/z) | 136.9570 | 132.4 | 0.05 | 128.8722 | 129.8759 | 126.8765 | 127.8779 | | | |
| 15 | Unknown (0.05_171.1493m/z) | 170.1421 | 137.3 | 0.05 | 128.8722 | 144.8659 | 170.8661 | 129.8739 | 126.8765 | 145.8685 | 156.8 |
| 16 | Unknown (0.05_223.2051m/z) | 222.1979 | 164.8 | 0.05 | 201.0462 | 202.0454 | 173.0507 | 173.8671 | 201.8626 | 217.8567 | 202.8 |
| 17 | Unknown (0.05_270.8859m/z) | 269.8787 | 133.7 | 0.05 | 172.8620 | 128.8722 | 144.8659 | 170.8661 | 173.8655 | 171.8398 | 129.8 |
| 18 | Unknown (0.05_279.0932m/z) | 278.0860 | 162.0 | 0.05 | 201.0462 | 279.0930 | 202.0494 | 171.0511 | 173.8671 | 274.7993 | 201.8 |
| 19 | Unknown (0.05_293.1129m/z) | 292.1057 | 163.2 | 0.05 | 201.0462 | 279.0930 | 202.0494 | 244.7911 | 91.0536 | 274.7993 | 290.7 |
| 20 | Unknown (0.05_329.8073m/z) | 328.8001 | 158.5 | 0.05 | 201.0462 | 279.0930 | 328.7914 | 202.0494 | 244.7911 | 171.0507 | 201.8 |
| 21 | Unknown (0.05_393.2963m/z) | 392.2891 | 217.8 | 0.05 | 311.1650 | 323.2564 | 312.1740 | | | | |
| 22 | Unknown (0.05_438.0655m/z) | 437.0587 | 188.1 | 0.05 | 334.0164 | 335.0192 | 335.0242 | 301.0769 | 363.7836 | 336.0293 | 144.8 |
| 23 | Unknown (0.06_216.5692m/z) | 215.8620 | 142.2 | 0.06 | 201.0461 | 172.8621 | 128.8722 | 144.8665 | 170.8661 | 202.0454 | 173.8 |
| 24 | Unknown (0.06_250.8309m/z) | 259.8717 | 140.2 | 0.06 | 172.8621 | 128.8722 | 144.8663 | 170.8661 | 218.5664 | 171.8654 | 91.0 |
| 25 | Unknown (0.06_467.8104m/z) | 466.8032 | 156.5 | 0.06 | 363.7868 | 319.7922 | 272.7943 | 172.0314 | 174.0540 | 272.7592 | 279.8 |
| 26 | Unknown (0.07_217.1053m/z) | 215.0981 | 142.2 | 0.07 | 172.8620 | 128.8717 | 144.5661 | 170.8561 | 129.8757 | 174.8647 | 171.8 |
| 27 | Unknown (0.07_278.9195m/z) | 277.9127 | 150.6 | 0.07 | 201.0462 | 173.8643 | 262.0492 | 229.1397 | 224.1282 | 245.7944 | 127.8 |
| 28 | Unknown (0.07_317.9348m/z) | 316.9276 | 154.0 | 0.07 | 201.0462 | 280.0959 | 218.8654 | 171.0509 | 202.0492 | 171.0345 | 229.1 |
| 29 | Unknown (0.07_354.3440m/z) | 393.3377 | 223.1 | 0.07 | 234.3449 | | | | | | |
| 30 | Unknown (0.08_230.8892m/z) | 229.8820 | 149.5 | 0.08 | 201.0462 | 172.8619 | 170.8657 | 144.8657 | 173.8660 | 218.8661 | 173.0 |
| 31 | Unknown (0.08_265.8651m/z) | 254.4579 | 140.0 | 0.08 | 172.8619 | 128.8718 | 170.8657 | 144.8657 | 218.4661 | 91.0540 | 229.1 |
| 32 | Unknown (0.08_406.7923m/z) | 405.7856 | 162.5 | 0.08 | 279.0930 | 318.7915 | 202.0490 | 218.8661 | 173.0512 | 171.0354 | 164.8 |
| 33 | Unknown (0.08_451.7879m/z) | 450.7807 | 164.6 | 0.08 | 318.7915 | 363.7864 | 173.0512 | 201.0154 | 359.2355 | 404.7837 | 290.7 |
| 34 | Unknown (0.09_211.8875m/z) | 212.5801 | 117.7 | 0.08 | 172.8620 | 128.8721 | 144.5661 | 170.8661 | 129.4238 | 174.8675 | 173.8 |
| 35 | Unknown (0.09_245.1111m/z) | 244.1041 | 153.6 | 0.09 | 201.0462 | 172.8621 | 171.0514 | 218.8660 | 244.7908 | 171.0358 | 164.8 |
| 36 | Unknown (0.09_319.9617m/z) | 318.9585 | 163.8 | 0.09 | 201.0462 | 318.7901 | 280.0963 | 244.7908 | 202.0416 | 171.0514 | 218.8 |
| 37 | Unknown (0.09_408.7852m/z) | 407.7730 | 154.7 | 0.09 | 201.0462 | 279.0927 | 311.7901 | 202.0486 | 173.0514 | 218.8660 | 171.0 |
| 38 | Unknown (0.09_452.3200m/z) | 451.1128 | 204.1 | 0.09 | 394.3483 | 395.3479 | 312.1665 | | | | |
| 39 | Unknown (0.010_245.0780m/z) | 244.0708 | 156.9 | 0.10 | 201.0462 | 202.0485 | 171.0509 | 171.0154 | 91.0537 | 244.7908 | 164.8 |
| 40 | Unknown (0.010_258.8831m/z) | 257.8759 | 140.3 | 0.10 | 201.0462 | 172.8619 | 128.8721 | 170.8664 | 202.0435 | 171.0509 | 171.0 |
| 41 | Unknown (0.010_260.5637m/z) | 259.8565 | 140.2 | 0.10 | 172.8619 | 128.8721 | 144.8665 | 229.1199 | 171.8616 | 154.8718 | 242.7 |

*FIG. 10*

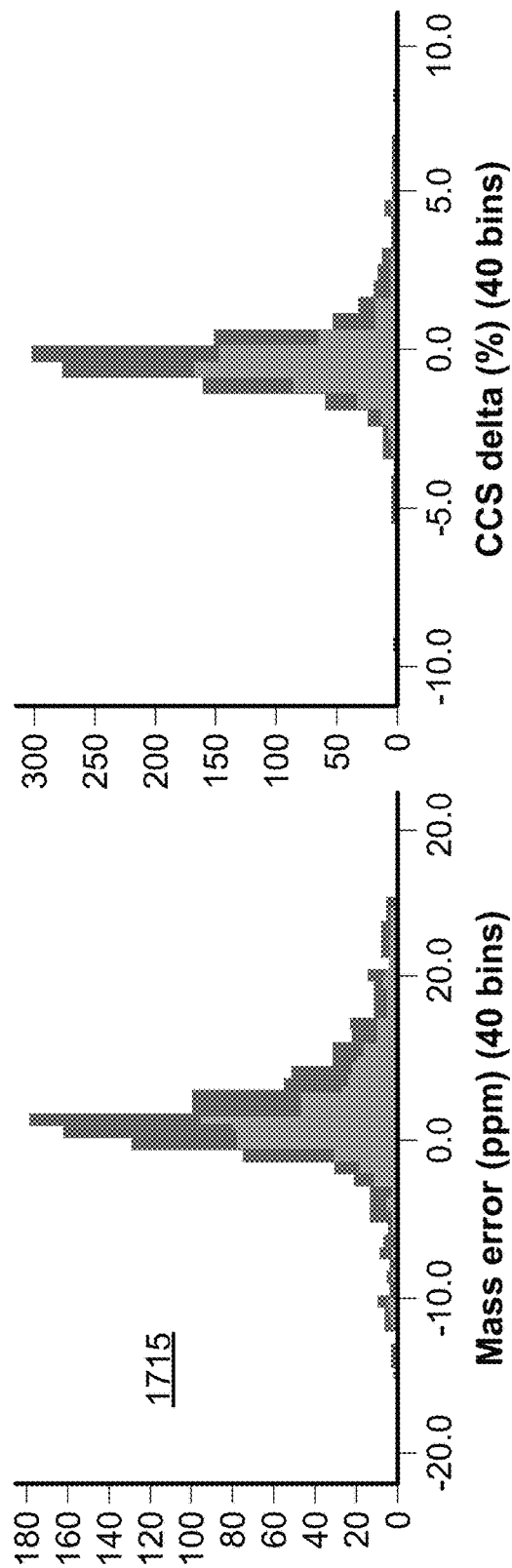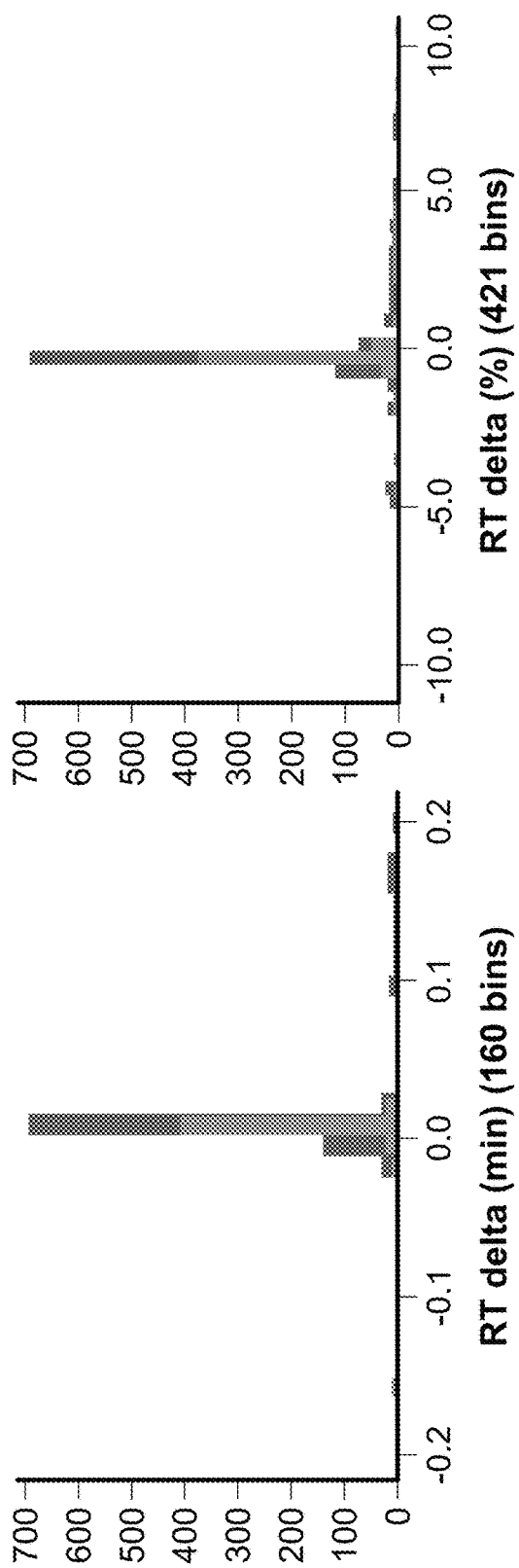
FIG. 17 (Cont. 1)

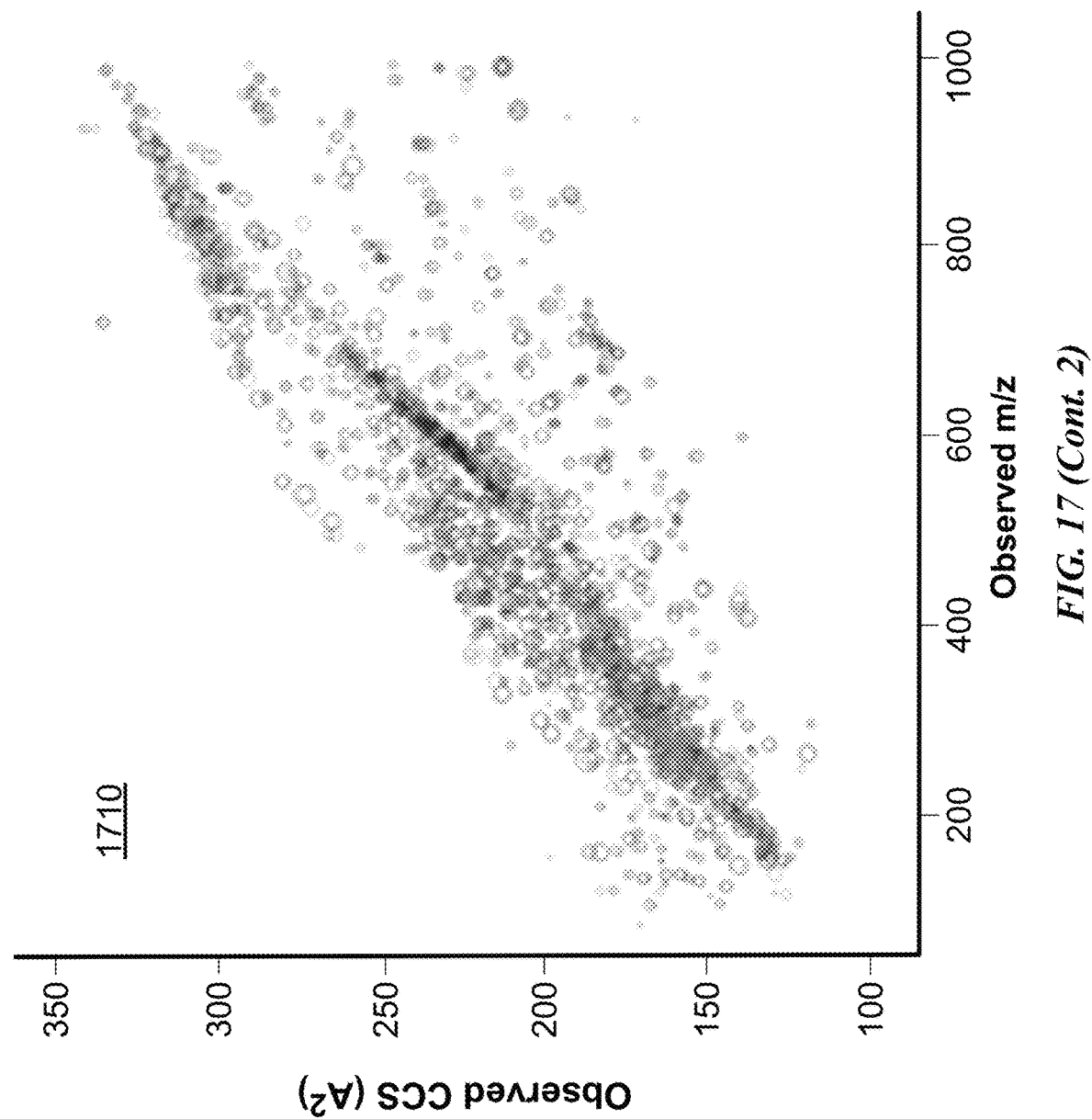
FIG. 17 (Cont. 2)

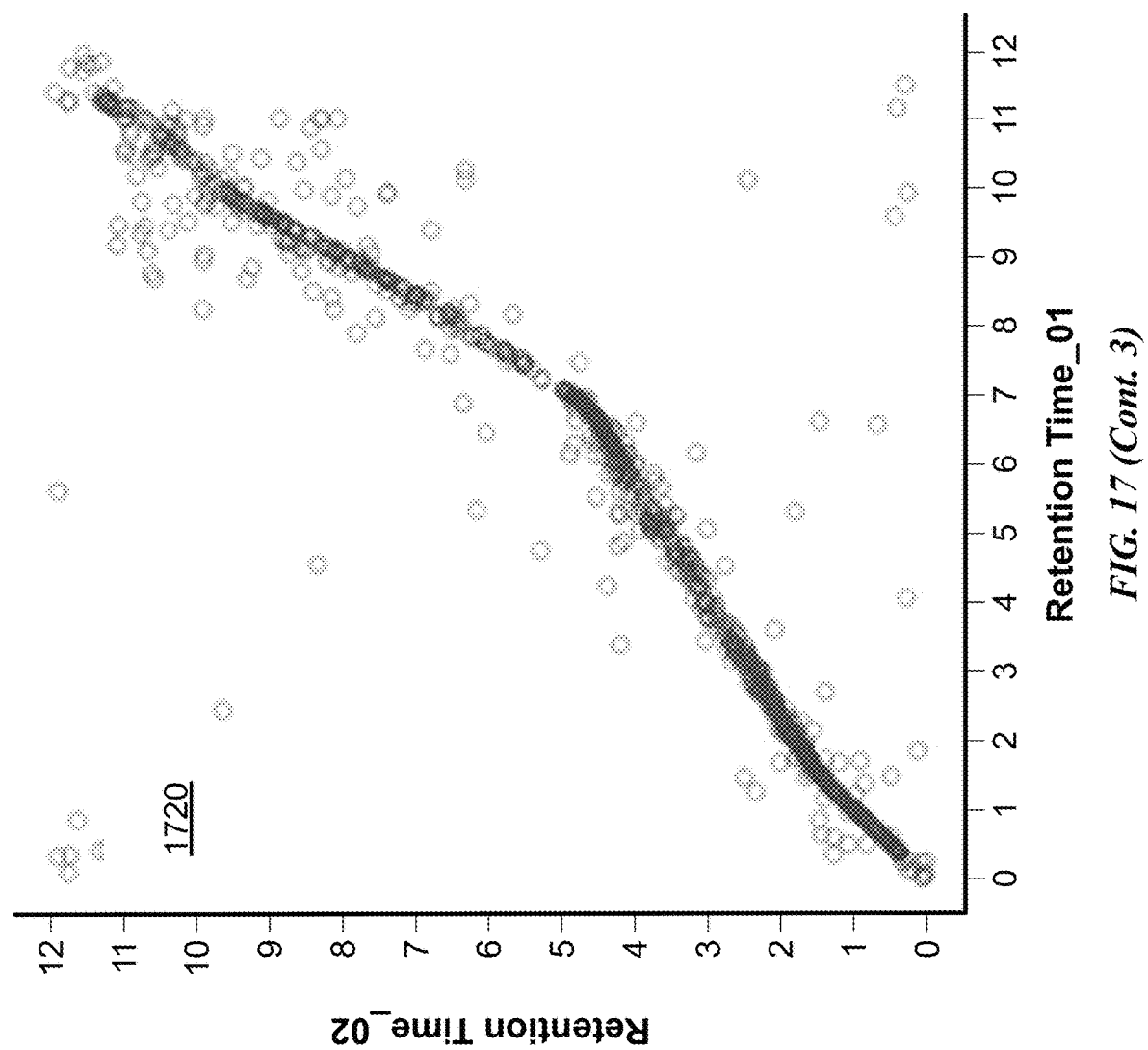
FIG. 17 (Cont. 3)

FIG. 21

TECHNIQUES FOR SAMPLE ANALYSIS USING CONSENSUS LIBRARIES

CROSS-REFERENCE TO RELATED APPLICATIONS

This application is a U.S. national phase filing claiming the benefit of and priority to International Patent Application No. PCT/GB2019/054556, filed on May 31, 2019, which claims priority from and the benefit of United Kingdom Patent Application No. 1809041.5, filed on Jun. 1, 2018. The entire contents of these applications are incorporated herein by reference.

TECHNICAL FIELD

Embodiments herein generally relate to mass analysis of samples, and, more particularly, to generating consensus libraries for sample matrices and using the consensus libraries to determine unknown and unidentified components of a sample.

BACKGROUND

A primary challenge in characterizing the components of a sample in an analytical analysis, such as mass spectrometry, is distinguishing components of interest from background signals. For example, analyzing the metabolic fate of xenobiotics requires distinguishing drug-related material in the presence of a complex set of background signals derived from the biological matrix in which metabolism has occurred, such as microsomes, hepatocytes, plasma, bile, or other matrices. Conventional methods operate to filter sample data by removing components found in a single control sample (binary comparison) and/or that are expected based on a structure of a compound (for instance, a drug) that is the subject of the analysis (for instance, product ions, biotransformations, and/or the like). However, such binary filtration is insufficient for complex sample matrices, particularly in vivo biological systems, where a large number of unknown data points still require detailed examination to determine their significance.

SUMMARY

In accordance with various aspects of the described embodiments, an apparatus may include at least one memory, and logic coupled to the at least one memory, the logic to receive a plurality of sample matrix data sets for a sample matrix generated via mass analysis of the sample matrix, and generate a consensus library for the sample matrix based on the plurality of sample matrix data sets, the consensus library comprising a plurality of known-unidentified components for the sample matrix.

In accordance with various aspects of the described embodiments, a computer-implemented method may include, by a processor of a computing device, receiving a plurality of sample matrix data sets for a sample matrix generated via mass analysis of the sample matrix; and generating a consensus library for the sample matrix based on the plurality of sample matrix data sets, the consensus library comprising a plurality of known-unidentified components for the sample matrix.

In some embodiments, mass analysis may be performed by at least one analytical instrument comprising at least one of a liquid chromatography (LC) system, a mass spectrometer (MS) system, an ion mobility spectrometer (IMS) system, a high-performance liquid chromatography (HPLC) system, an ultra-performance liquid chromatography (UPLC) system, an ultra-high performance liquid chromatography (UHPLC) system. In various embodiments, mass analysis may be performed by a liquid chromatography (LC)-ion mobility spectrometer (IMS)-mass spectrometer (MS) system.

In some embodiments, the sample matrix may include one of a biological matrix, an environmental matrix, or a chemical matrix. In exemplary embodiments, the plurality of sample matrix data sets may include at least one of mass-to-charge ratio (m/z), retention time, drift time, product ions, or collision cross section (CCS) information. In some embodiments, the plurality of sample matrix data sets may include mass-to-charge ratio (m/z), retention time, and collision cross section (CCS) information. In various embodiments, the consensus library may include known-identified components of the sample matrix. In various embodiments, at least a portion of the plurality of known-unidentified components may include native components of the sample matrix with an unidentified structure. In various embodiments, unidentified may include an unknown structure, a tentative structure, and/or an elemental composition without a known structure. In some embodiments, the matrix may include materials used in an analysis of a sample for that type of matrix, such as reagents, controls, standards, chemical compounds, and/or the like. Accordingly, in various embodiments, native components of a matrix for purposes of generating a component library may include non-natural components of a matrix that are nonetheless considered native as they are present under analytical conditions.

In some embodiments, the consensus library may include an incidence rate for each of the plurality of known-unidentified components. In some embodiments, the consensus library may include component characteristics for at least a portion of the plurality of known-unidentified components. In some embodiments, the consensus library may include component characteristics for at least a portion of the plurality of known-unidentified components, the component characteristics comprising at least one of mass-to-charge (m/z) ratio, retention time, collision-cross section (CCS) information, and fragment information. In various embodiments, a known-unidentified component may be included in the plurality of known-unidentified components of the consensus library responsive to the known-unidentified component having a component characteristic over a threshold value. In some embodiments, the threshold value may include at least one of a minimum concentration or a minimum incidence rate.

In some embodiments, a sample analysis data set may be received that is generated via mass analysis of a sample associated with the sample matrix, and an unknown-unidentified data set for the sample may be generated via comparing the sample analysis data set with a consensus library for the sample matrix. In various embodiments, the comparison may be based on mass-to-charge ratio (m/z) and collision cross section (CCS) information of the sample analysis data set.

In accordance with various aspects of the described embodiments, an apparatus may include at least one memory, and logic coupled to the at least one memory, the logic may receive a sample data set generated via mass analysis of a sample associated with a sample matrix, and generate an unidentified component list for the sample by filtering out known-unidentified components of the sample data set via comparing the sample data set to a consensus library comprising a plurality of known-unidentified components for the sample matrix.

In accordance with various aspects of the described embodiments a computer-implemented method may include, by a processor of a computing device, receiving a sample data set generated via mass analysis of a sample associated with a sample matrix, and generating an unidentified component list for the sample by filtering out known-unidentified components of the sample data set via comparing the sample data set to a consensus library comprising a plurality of known-unidentified components for the sample matrix.

In some embodiments, the consensus library may be updated based on the sample data set. In various embodiments, mass analysis may be performed by at least one analytical instrument comprising at least one of a liquid chromatography (LC) system, a mass spectrometer (MS) system, an ion mobility spectrometer (IMS) system, a high-performance liquid chromatography (HPLC) system, an ultra-performance liquid chromatography (UPLC) system, or an ultra-high performance liquid chromatography (UHPLC) system. In some embodiments, mass analysis may be performed by a liquid chromatography (LC)-ion mobility spectrometer (IMS)-mass spectrometer (MS) system.

In various embodiments, the sample matrix may include one of a biological matrix, an environmental matrix, or a chemical matrix. In various embodiments, the unidentified component list may be generated based on at least one of of mass-to-charge ratio (m/z), retention time, drift time, product ions, or collision-cross section (CCS) information of the sample data. In exemplary embodiments, the unidentified component list may be generated based on mass-to-charge ratio (m/z) collision-cross section (CCS), retention time, and tandem mass spectrometry (MS/MS) information of the sample data. In various embodiments, the consensus library may include known-identified components of the sample matrix.

DETAILED DESCRIPTION

Figure 1:
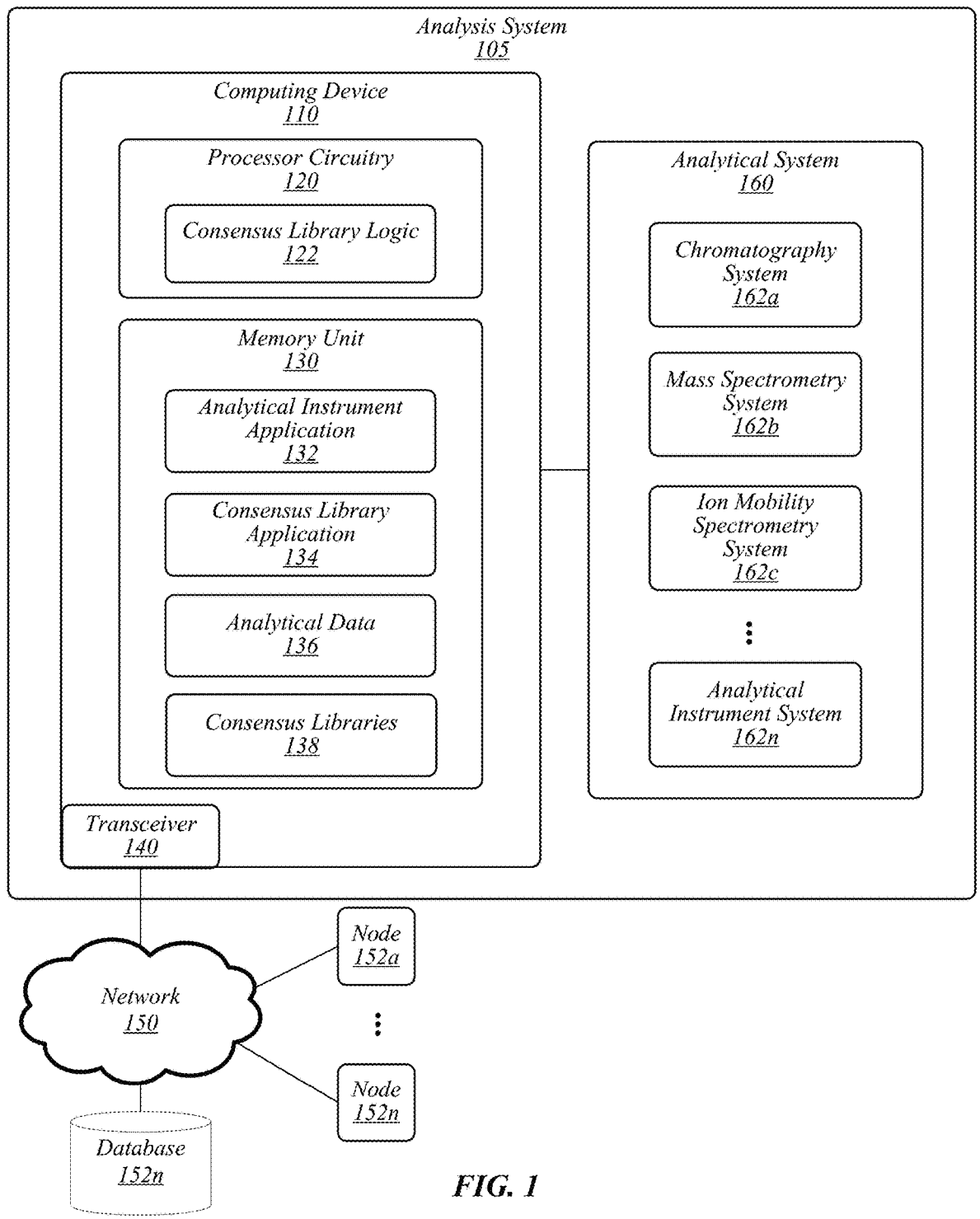
FIG. 1 illustrates an embodiment of a first operating environment.

Various embodiments may generally be directed toward systems, methods, and/or apparatus for determining components of interest of a sample using one or more consensus libraries of native components of one or more matrices associated with the sample. In some embodiments, sample matrices may be analyzed to determine native components of the sample matrices. Consensus libraries for the sample matrices may be generated to store information for the native components. Analytical data obtained by analysis of the sample may be processed using the consensus library to determine native and non-native components of the sample. In this manner, analysis of the sample to determine components of interest (for instance, components that are associated with the results of an experiment) may focus efficiently on the non-native components, while removing the native components (for instance, background matrix components) from consideration.

One of the primary challenges in characterizing the metabolic fate of xenobiotics is distinguishing drug-related material in the presence of a complex set of background signals derived from the biological matrix in which metabolism has occurred. Non-limiting examples of such biological matrices may include microsomes, hepatocytes, plasma, bile, and/or the like. One conventional approach is to filter components based on properties related to the parent drug, for instance, based on isotope patterns, common product ions, neutral losses, biotransformations which are expected based on the structure of the drug, combinations thereof, and/or the like. However, such conventional approaches typically fail to identify "unexpected metabolites," components which are drug-related, but for a variety of reasons may not be identified using conventional filtering processes. Another conventional method is to look at components which are only present in analyte samples, and not in controls. However, the nature of complex biological systems, particularly in vivo, is such that this approach may still leave many hundreds of analyte-specific peaks to be inspected.

Accordingly, conventional analysis methods primarily operate by attempting to remove natively present components from consideration using a single, pairwise comparison of each sample with a standard, generic control (for example, one in which no drug was added, or co-factors were removed, or the sample was quenched before metabolism can occur, and/or the like). Such approaches are inefficient and ineffective because matrices, such as biologically active systems, undergo a variety of processes over time, resulting in false positive detections corresponding to the new molecular entities which are formed by these processes, and which are not present in the control sample.

Accordingly, in some embodiments an analysis process is provided to make this challenge more tractable, for example, by characterizing and capturing the native complement of a matrix (such as a biological matrix) in a library based on one or more of a plurality of characteristics of matrix components (for instance, mass to charge ratio (m/z), collision cross section (CCS), product ions, drift time, retention time, combinations thereof, and/or the like) to generate a consensus library for the matrix that flags components in analyte samples that are known to be natively present, and thus are unlikely to be a component of interest (for example, a drug metabolite).

By definition, a drug metabolite is not expected to be an endogenous component of a native biological matrix. Various embodiments provide a process operative to enable a complete characterization of all samples within an analysis set, in order to define a consensus library of endogenous components (for instance, m/z, CCS, product ion data), which are systematically present within those samples. In exemplary embodiments, within the library, the occurrence rates of each component within the sample set are captured. In various embodiments, the occurrence rate captured for each component within the sample may allow for systematically evaluation of the novelty of each component to determine, for example, how frequently does each component appear within the history of all analyses of the subject matrix.

Figure 6:
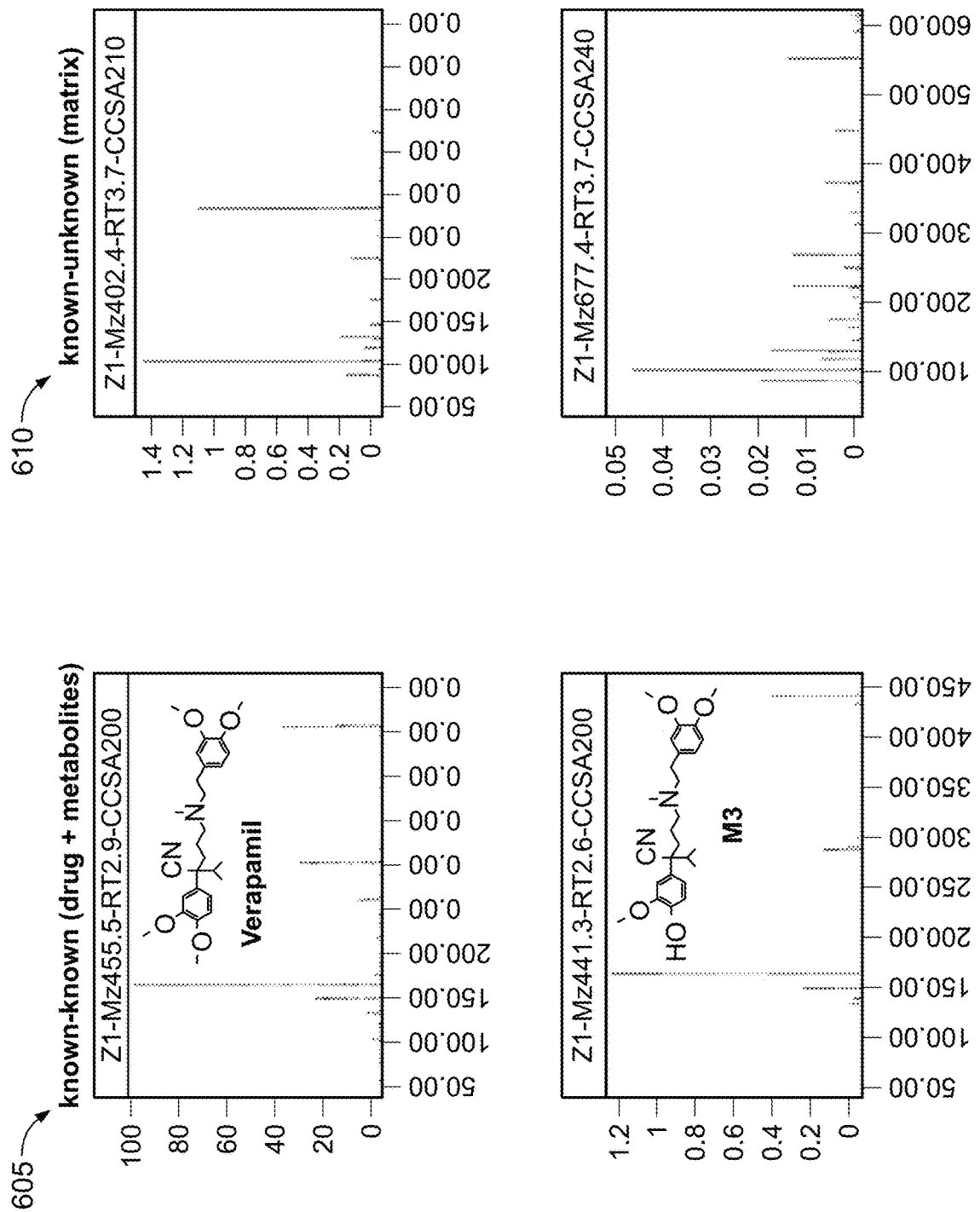

The result of this analysis is a consensus library that includes set of known-identified components (or "known-knowns," which are known components with known structures) and/or known-unidentified components (or "known-unknowns," which have an indeterminate structure, but which are known to be from the matrix across a variety of conditions) (see, for example, 605 and 610 of FIG. 6, respectively, for examples of known-known and known-unknown components). In some embodiments, the consensus library may be used, for example, within a targeted screening workflow to evaluate all components for a match with the consensus background (for instance, rather than performing a simple, inefficient binary compare with a single control sample according to conventional processes).

In comparison to a conventional binary compare approach, processes according to some embodiments which use consensus library-based process result in a significantly greater enrichment rate (n[true positives]/n[total components]). Accordingly, processes according to some embodiments represent more efficient and effective analysis processes, saving time and resources. In addition, some embodiments may operate to create self-learning workflows, in which each additional sample measured can be used to improve the consensus libraries associated with a matrix.

Although some embodiments may use drug metabolism as an example, embodiments are not so limited as the processes described may be used to identify non-native components that are not part of the native, consensus background of any matrix and/or analysis category capable of operating according to various embodiments. Non-limiting examples may include drug impurity characterization, food speciation/storage analysis, chemical and (bio)pharmaceutical fingerprinting, biomedical research experiments, water/groundwater testing, soil testing, and/or the like.

For example, in metabolomics (including lipidomics, fluxomics and large scale phenotyping), some embodiments may provide processes for metabolites and/or metabolomic pathway up/down regulation in response to treatment, control, knockout, combinations thereof, and/or the like. In such experimental approaches, treatment groups may exhibit differences in compound presence/absence or concentration that do not arise from the drug of interest (for instance, secondary or tertiary processes in response to treatment).

Additional illustrative and non-limiting examples may include food and environmental applications, authentication, profiling, and/or the like, speciation (for instance, determining components of a species, such as profiling flavonoids of the *Passiflora* species using ion mobility separation, to enhance specificity of authentication profiling), speciation (for instance, meat products, fish products, and/or the like using direct analysis (for example, Rapid Evaporative Ionization Mass Spectrometry REIMS)), food ageing (for instance, time of harvest, and/or the like), food storage (for instance, profiling of chemical profile of a food product, monitoring the fingerprint to determine any change with age, this can also relate to food taint, whereby the cause of food taint may not be known, but a chemical finger print could be obtained, neutraceuticals (for instance, chemical finger profiling for fake products, product purity, compare with expected chemical finger print, and/or the like), pharmaceuticals (for instance, determining pharmaceutical fingerprint, profiling fingerprint for fake products, product purity, comparison to expected chemical fingerprint), food processing (for instance, product processing (for example, creating a coffee roasting processing system) and/or monitoring to obtain the same chemical fingerprint, identifying unexpected components which are not part of the consensus fingerprint, and/or the like), biotransformation products (for instance, monitor a chemical fingerprint of biotransformation products for various applications, such as application of pesticides to food, administration of veterinary drugs to animals, and/or the like), forensic toxicology (for instance, identification of novel components which are not part of the consensus background of urine, plasma, and/or the like, and do not match with a library of known drugs), and/or the like. Embodiments are not limited in this context.

In this description, numerous specific details, such as component and system configurations, may be set forth in order to provide a more thorough understanding of the described embodiments. It will be appreciated, however, by one skilled in the art, that the described embodiments may be practiced without such specific details. Additionally, some well-known structures, elements, and other features have not been shown in detail, to avoid unnecessarily obscuring the described embodiments.

In the following description, references to "one embodiment," "an embodiment," "example embodiment," "various embodiments," etc., indicate that the embodiment(s) of the technology so described may include particular features, structures, or characteristics, but more than one embodiment may and not every embodiment necessarily does include the particular features, structures, or characteristics. Further, some embodiments may have some, all, or none of the features described for other embodiments.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner.

FIG. 1 illustrates an example of an operating environment 100 that may be representative of some embodiments. As shown in FIG. 1, operating environment 100 may include an analysis system 105 operative to manage analytical data associated with analytical system 160. In some embodiments, analytical system 160 may include one or more analytical instrument systems 162*a-n* operative to perform mass analysis on a sample. In various embodiments, analytical instrument systems 162*a-n* may be or may include a chromatography system, a liquid chromatography (LC) system, a gas chromatography (GC) system, a mass analyzer system, a mass spectrometer (MS) system, an ion mobility spectrometer (IMS) system, a high definition mass spectrometer (HDMS) system, a time-of-flight (TOF) MS system, an MS system operated in a data-dependent mode, an MS system operated in a data independent, an MS system operated in an MS of everything (MSe or HDMSe) mode, a high-performance liquid chromatography (HPLC) system, a ultra-performance liquid chromatography (UPLC®) system, a ultra-high performance liquid chromatography (UHPLC) system, a solid-phase extraction system, a sample preparation system, combinations thereof, components thereof, variations thereof, and/or the like. In some embodiments, any of analytical instrument systems 162*a-n* may operate in combination. Although LC, MS, LC-MS, MS-MS (tandem MS), IMS-MS, and HDMSe are used in examples in this detailed description, embodiments are not so limited, as other analytical instruments and/or operating modes capable of operating according to some embodiments are contemplated herein.

In some embodiments, analytical instrument systems 162a-n may operate to perform an analysis. For example, for an LC-MS system, analytical instrument systems 162a and 162b may operate to separate a sample and perform mass analysis on the separated sample to generate analytical data 136 that may include, for instance, spectra information, retention time t(r) information, and/or the like. In another example, for an LC-MS-IMS system, analytical instruments 162a-c may operate to separate a sample and perform mass analysis and ion mobility analysis on a sample to generate analytical data 136 that may include, for instance, spectra information, t(r), collision cross section (CCS) information, drift time (t(d)) information, and/or the like. In some embodiments, analytical data 136 may include data from historical or database analyses, such as spectral databases, peptide libraries, protein libraries, standard reference material data, pharmaceutical databases, drug interaction databases, metabolic databases, proteomic databases, and/or the like. Embodiments are not limited in this context.

In various embodiments, analysis system 105 may include computing device 110 communicatively coupled to analytical system 162, one or more of analytical instrument systems 162a-n, and/or otherwise configured to receive and store analytical data 136. For example, analytical instrument 162b may operate to provide analytical data to a location on a network 150 (for instance, a cloud computing environment or analytical instrument management platform) accessible to computing device 110. In some embodiments, computing device 110 may be operative to control, monitor, manage, or otherwise process various operational functions of analytical instrument 115. For example, in various embodiments, computing device 110 may execute an analytical instrument application 132 operate to control various functions of one or more of analytical instrument systems 162a-n. For instance, analytical instrument application 132 may operate as a control interface for analyzing samples on analytical instrument systems 162a-n, receiving and/or processing analytical data from analytical instrument systems 162a-n, and/or the like. Non-limiting examples of analytical instrument applications 132 may include chromatography data software (CDS), mass spectrometry software, lab management software, LC-MS data analysis software, databases (for instance, mass spectral databases, proteomics databases, protein identification databases, and/or the like. Further illustrative and non-restrictive examples of analytical instrument applications 132 may include Empower™ (for instance, Empower™ 3) CDS, MassLynx™ Mass Spectrometry Software, Progenesis™ QI LC-MS data analysis software, and UNIFI™ scientific information system developed by Waters Corporation of Milford, Massachusetts, United States of America. Embodiments are not limited in this context.

In some embodiments, computing device 110 may be or may include a stand-alone computing device, such as a personal computer (PC), server, tablet computing device, cloud computing device, and/or the like. In various embodiments, computing device 110 and/or portions or components thereof may be a component of one or more of analytical instrument systems 162a-n.

As shown in FIG. 1, computing device 110 may include processing circuitry 120, a memory unit 130, and a transceiver 140. Processing circuitry 120 may be communicatively coupled to memory unit 130 and/or transceiver 140. Processing circuitry 120 may include and/or may access various logic for performing processes according to some embodiments. For instance, processing circuitry 120 may include and/or may access consensus library logic 122. Processing circuitry and/or consensus library logic 122, or portions thereof, may be implemented in hardware, software, or a combination thereof. As used in this application, the terms "logic," "component," "layer," "system," "circuitry," "decoder," "encoder," and/or "module" are intended to refer to a computer-related entity, either hardware, a combination of hardware and software, software, or software in execution, examples of which are provided by the exemplary computing architecture 1900. For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

Although consensus library logic 122 is depicted in FIG. 1 as being within processing circuitry 120, embodiments are not so limited. For example, consensus library logic 122 may be located within an accelerator, a processor core, an interface, an individual processor die, implemented entirely as a software application (for instance, consensus library application 134) and/or the like.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store a consensus library application 134 that may, when executed by computing device 110, operate, alone or in combination with consensus library logic 122, to perform various processes according to some embodiments. For example, consensus library application 134 may generate a consensus library 138 stored locally in memory unit 130 and/or on a node 152a-n of network 150. Although consensus library application 134 and analytical instrument application 132 are depicted as separate applications (and/or logic) in FIG. 1, embodiments are not so limited. For example, consensus library application 134 may be a module or component of analytical instrument application 132 and vice versa.

Analytical instrument systems 162a-n may analyze samples of a particular sample type, category, origin, analytical process, study, or "matrix." In general, a matrix is a classification of a sample based on the type of sample and/or the analytical process or experiment associated with the sample. Non-limiting examples of sample matrices may include biological matrices (for instance, blood, serum, plasma, urine, cells (for instance, cells of a particular organ or type, such as tumor cells), and/or the like), environmental matrices (for instance, water, ground water, soil, air, and/or the like), chemical matrices (for instance, chemical products, intermediaries, source materials, and/or the like), metabolic matrices, combinations thereof, and/or other types of matrices. In addition, a sample matrix may include a type of study or experiment associated with a sample. Non-limiting examples of such matrices may include metabolomics, lipidomics, fluxomics, phenotyping, proteomics, speciation, contamination studies, toxicology screenings, pesticide screenings, bioanalysis, and/or the like. Embodiments are not limited in this regard.

In exemplary embodiments, consensus library application 134 may operate to generate consensus libraries 138 for various matrices. For example, in some embodiments, one or more types of matrices (which may include types, categories, or other variations of a particular matrix) of samples analyzed by one or more of analytical instrument systems 162a-n may have a corresponding consensus library 138.

In general, each type of matrix (for instance, human plasma, ground water, and/or the like) may have a complement of native components that exist within each sample of that type of matrix (for example, endogenous components for a biological matrix). The native components are always or substantially always present within a sample from that particular type of matrix. The purpose of the sample analysis is to locate non-native components that are not always or substantially always present within the particular type of matrix for that sample. For example, with a metabolic study within a human plasma matrix for a particular drug, the native components are the endogenous components of plasma and the non-native components may be related to metabolism of the particular drug.

According to some embodiments, consensus library application may operate to analyze analytical data resulting from analyzing a sample (for instance, spectra resulting from mass analysis of a human plasma sample) to determine known-identified ("known-knowns"), known-unidentified ("known-unknowns"), and unknown-unidentified ("unknown-unknowns") components. Known-identified components may be known and identified, for example, from previous analysis of samples of this type of matrix (for instance, identifiable from a database of historical analytical data). Known-unidentified components may include components that are native components of the matrix, but whose particular structure is unknown. For example, known-unidentified components may include components of low concentration, components that exist sporadically within a matrix, or for other reasons do not have an identified structure for a particular matrix. Unknown-unidentified components may include non-native components of the matrix that are unique to the sample.

In general, sample analyses are focused on determining the structure of unknown-unidentified components. However, conventional systems do not account or do not adequately account for known-unidentified components of a matrix. As a result, conventional systems identify or flag known-unidentified components as false positives (for instance, as false unknown-unidentified components), and time and resources are allocated to determining the exact composition of known-unidentified components of a matrix. Accordingly, consensus library application 134 according to some embodiments may generate consensus libraries 138 for matrices that include known-unidentified components (as well as, in some embodiments, known-identified components). In exemplary embodiments, a consensus library 138 may also include other information associated with known-unidentified components, such as component characteristics (for instance, m/z, retention time, drift time, and/or the like), concentration levels, intensity levels, incident rates, and/or the like. For example, the incidence or occurrence rate captured for each known-unidentified component within the sample for systematic evaluation of the novelty of said components (for instance, to determine the frequency that a known-unidentified component appears with the historical data for analysis of the corresponding matrix or variations thereof).

In this manner, a consensus library 138 may include a set of "known-unknowns," that may be components which have an indeterminate structure, but which are known to be from the particular matrix across a variety of conditions. In various embodiments, a consensus library 138 may be used as part of a targeted screening workflow to filter out all native components of a matrix, for example, to facilitate detection of non-native components that exist within a sample.

Figure 2:
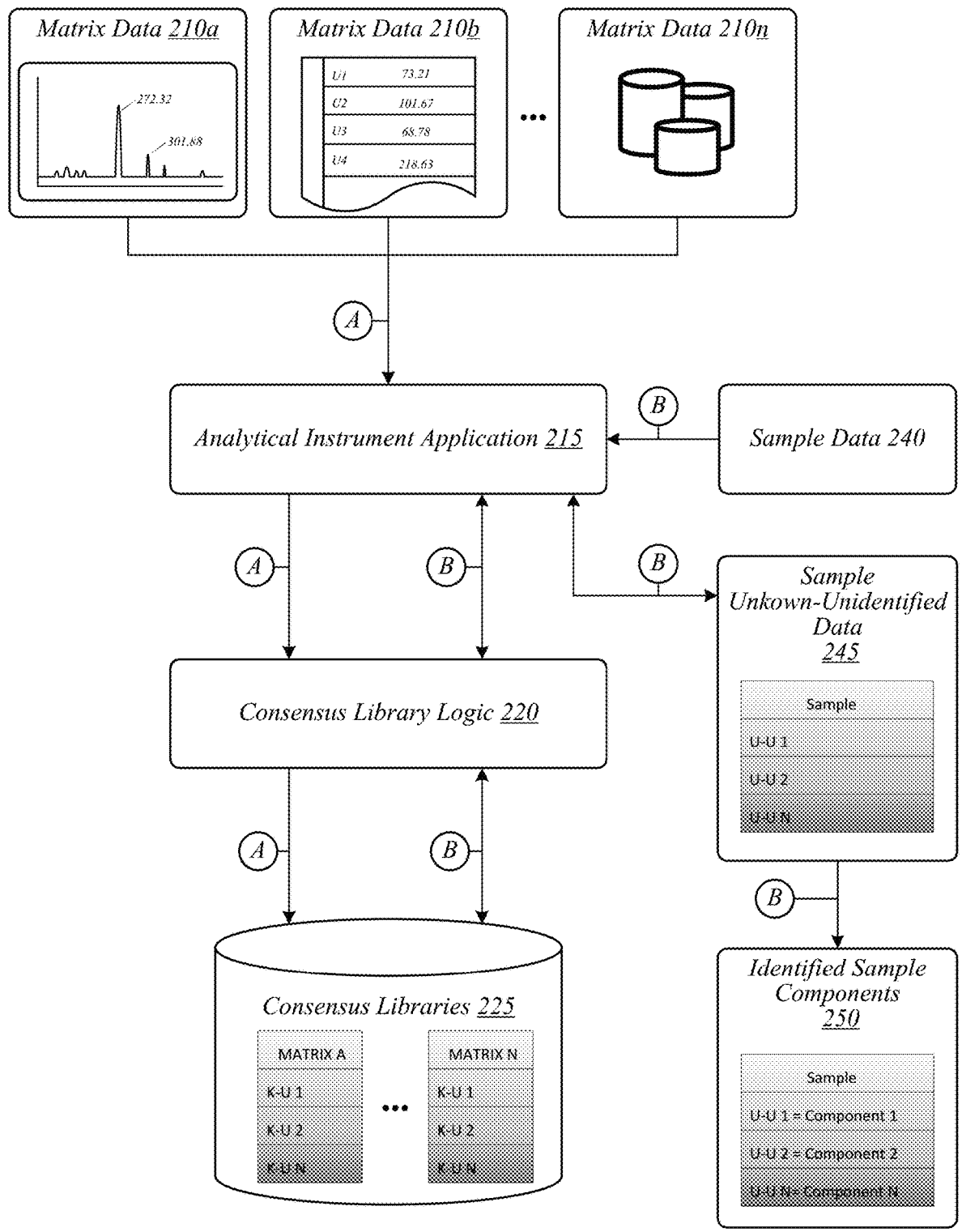
FIG. 2 illustrates an embodiment of a first logic flow according to some embodiments.

FIG. 2 illustrates an example of illustrative workflow or logic flow 200 that may be representative of some embodiments. Logic flow 200 may be representative of some or all of the operations executed by one or more embodiments described herein, such as analysis system 105 and/or computing device 110. As shown in FIG. 2, workflow 200 may include flow A for generating consensus libraries and flow B for using consensus libraries to identify unknown-unidentified components in a sample.

Flow A may begin by receiving matrix data 210a-n for a matrix. For example, matrix data 210a-n may include data for one or more component characteristics of the matrix generated by a plurality of analysis of the matrix. Illustrative component characteristics may include m/z, retention time, drift time, CCS, product ions, and/or the like. Matrix data 210a-n may be generated using a matrix in a standard form, for instance, in a native form unchanged by experimental components. For example, for a metabolic study using hepatocyte cells, the matrix may be hepatocyte cells of the subject prior to application of a pharmaceutical. The matrix data 210a-n may be generated by performing one or a plurality of analysis of the matrix in the standard form. For example, matrix data 210a-n may be generated by performing a plurality of LC-MS experiments of the matrix, including under different conditions (for instance, incubation conditions, analysis gradients, analysis parameters, and/or the like).

In various embodiments, matrix data 210a-n may be received by an analytical instrument application 215. For example, data from LC-MS, MS-IMS, and/or the like may be generated by or otherwise provided to Progenesis™ QI, UNIFI™, and/or similar software to process the matrix data 210a-n. For example, analytical instrument application 215 may operate to remove background noise, improve data signal-to-noise ratio (SNR), data/feature alignment, data/feature aggregation, feature extraction, feature detection, feature quantification, feature inspection, normalization, deconvolution, data filtering, statistical analysis, signal integration, combinations thereof, and/or the like. Embodiments are not limited in this context.

In various embodiments, matrix data 210a-n may be provided to consensus library logic 220. In exemplary embodiments, consensus library logic 220 may determine a matrix associated with received matrix data 210a-n. For example, matrix data 210a-n may be associated with cells from a particular species (for instance, human hepatocytes), particular subject (for instance, specific patient), certain conditions (for instance, human hepatocytes from a cancerous liver), analytical conditions (for instance, particular instrument, operating parameters, and/or the like), combinations thereof, and/or the like. In general, a matrix may be classified according to any type of classification process, for example, that may be user-defined and/or defined by consensus library logic 220, for instance, according to an automated classification process. Embodiments are not limited in this context.

Consensus library logic 220 may analyze matrix data 210a-n to determine components that are consistently detected across all or a threshold number of analysis runs with regard to one or more component characteristics. For example, consensus library logic 220 may determine components that are consistently detected across a threshold number of a plurality of runs with regard to m/z, retention time, drift time, and/or CCS. In some embodiments, certain component characteristics may be used to detect components and certain other component characteristics may be used to validate detected components. For example, m/z and retention time may be used to detect components and CCS may be used to validate the detection of the components.

Figure 4:
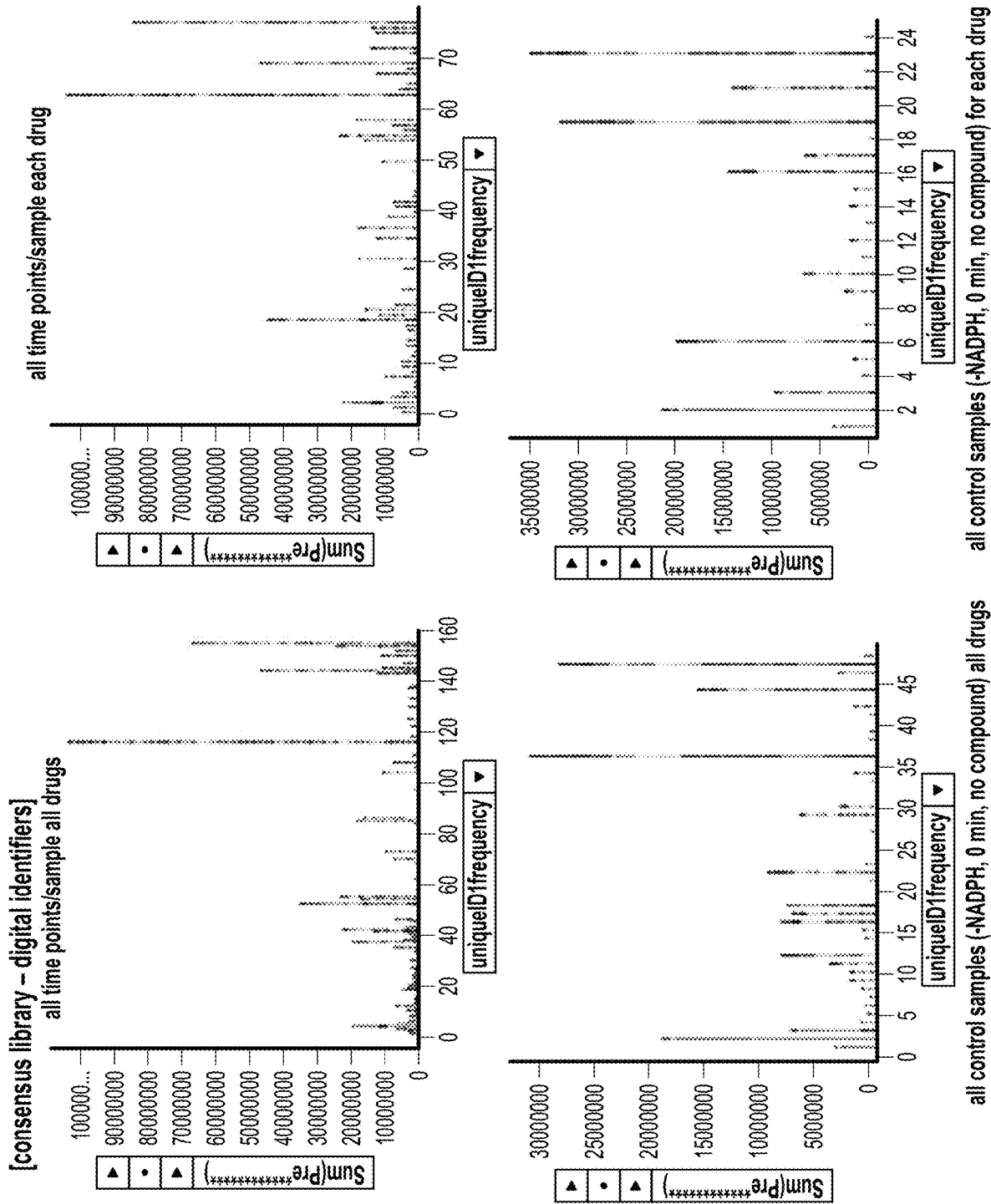
FIGS. 4-7 illustrates example consensus library information according to some embodiments.
Figure 4:
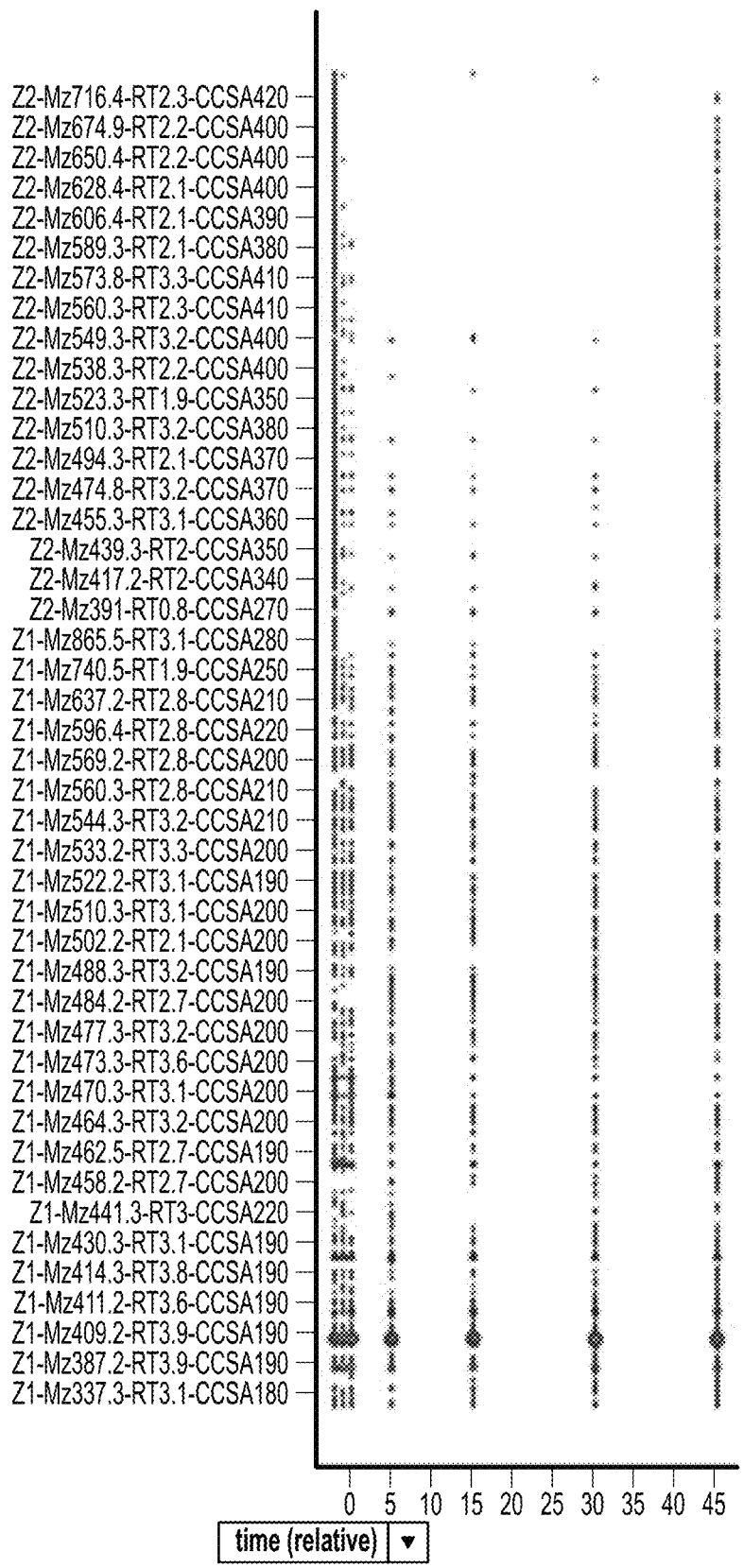
Figure 5:
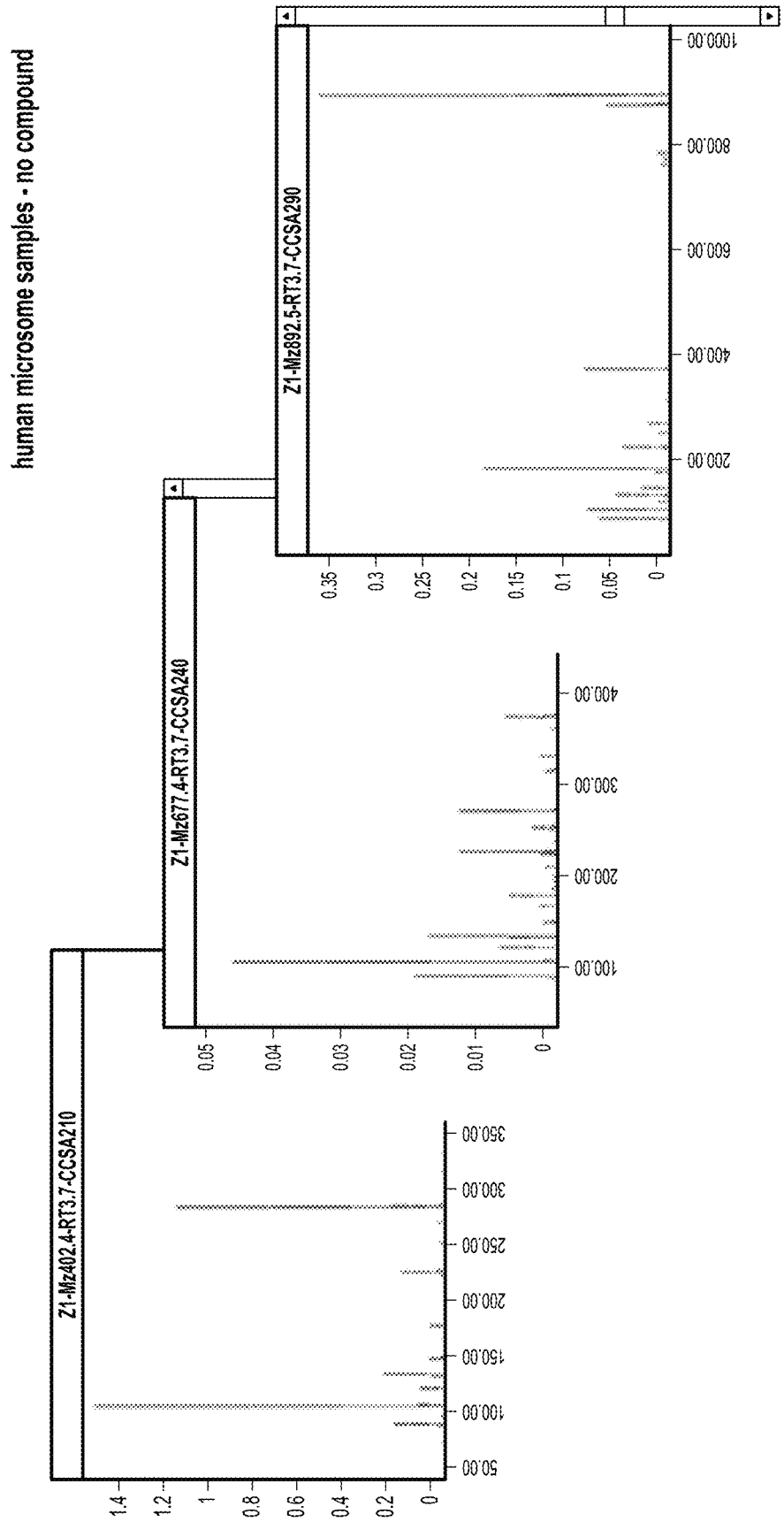
Figure 5:
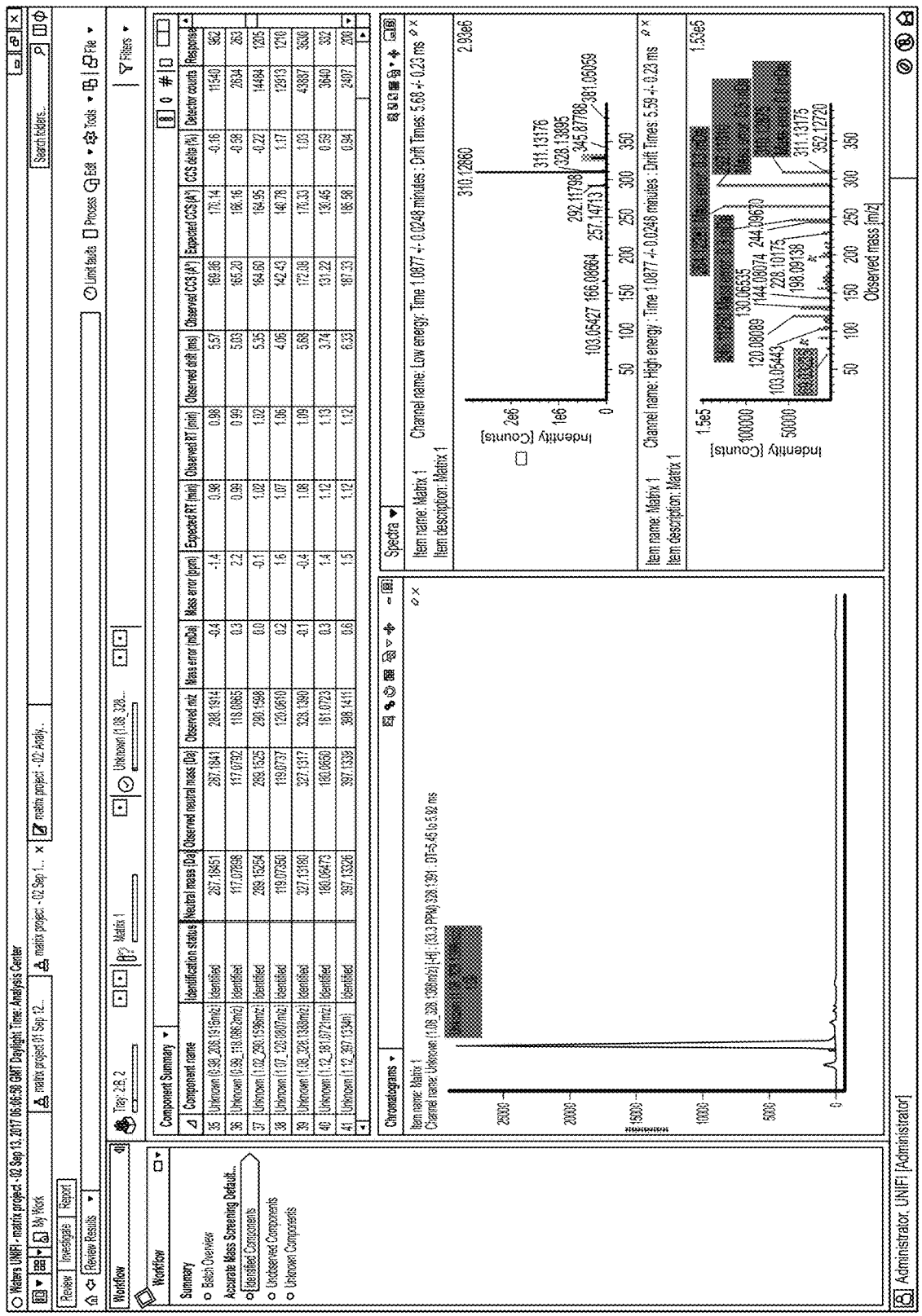
Figure 7:
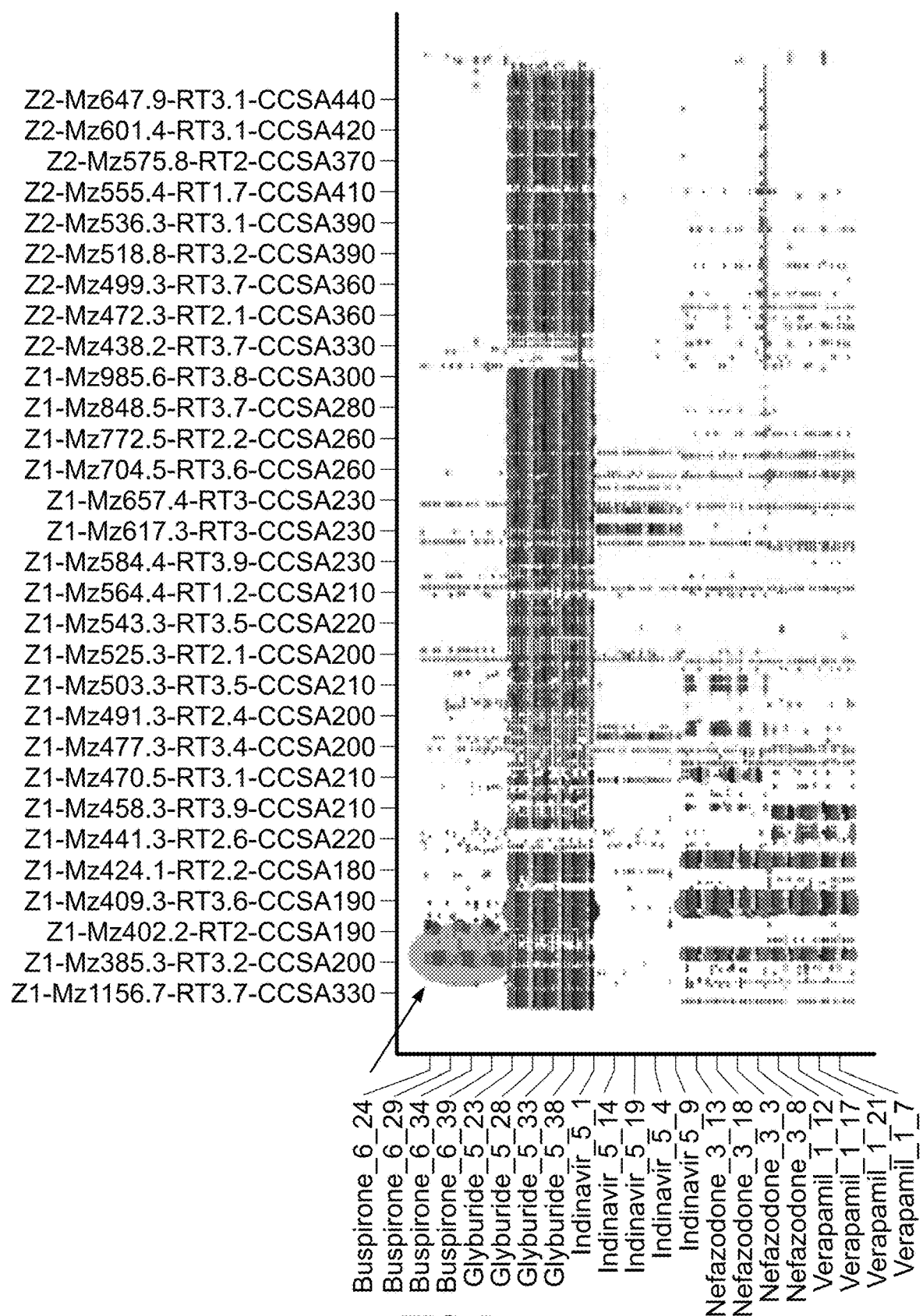
Figure 7:
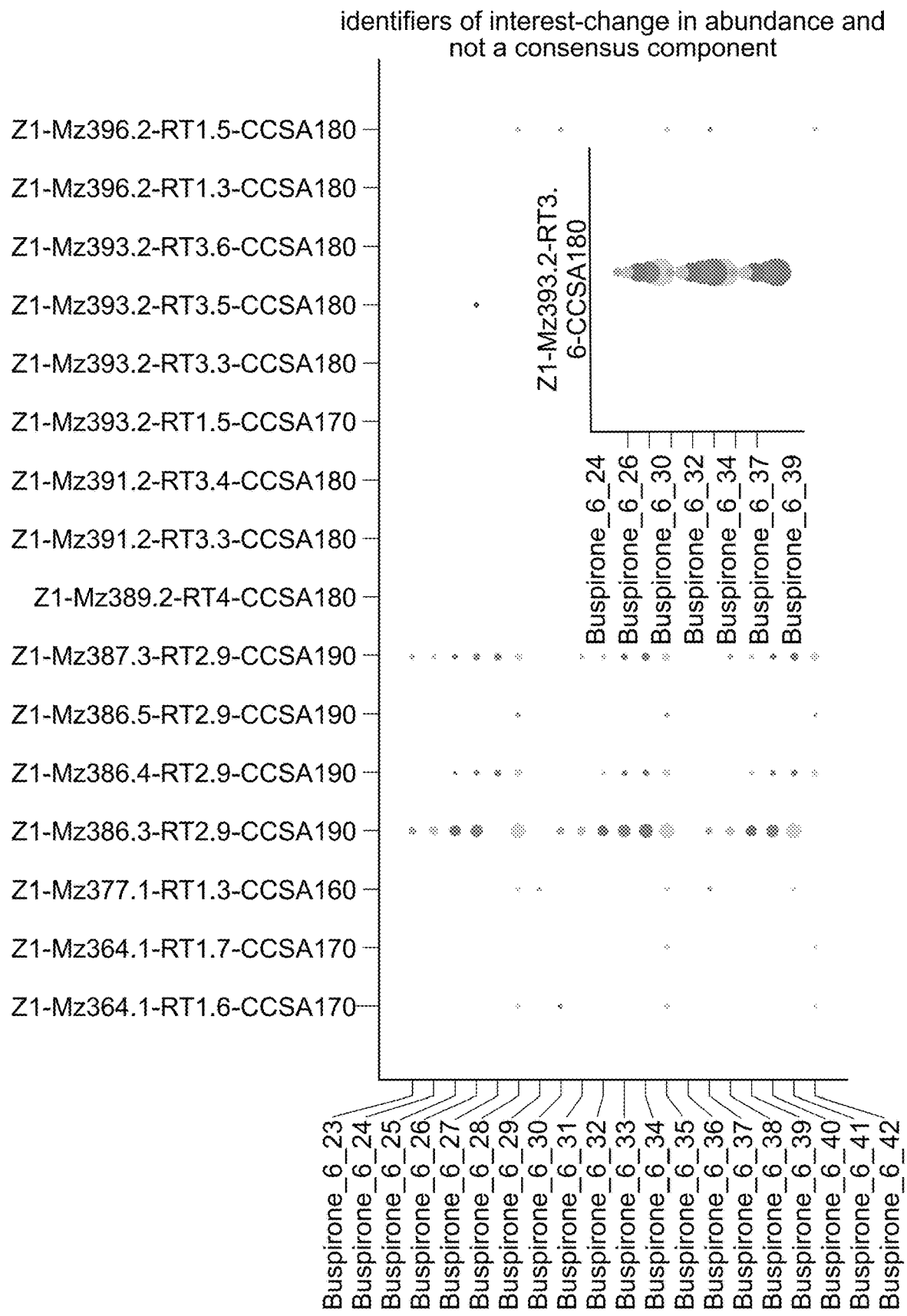
Figure 7:
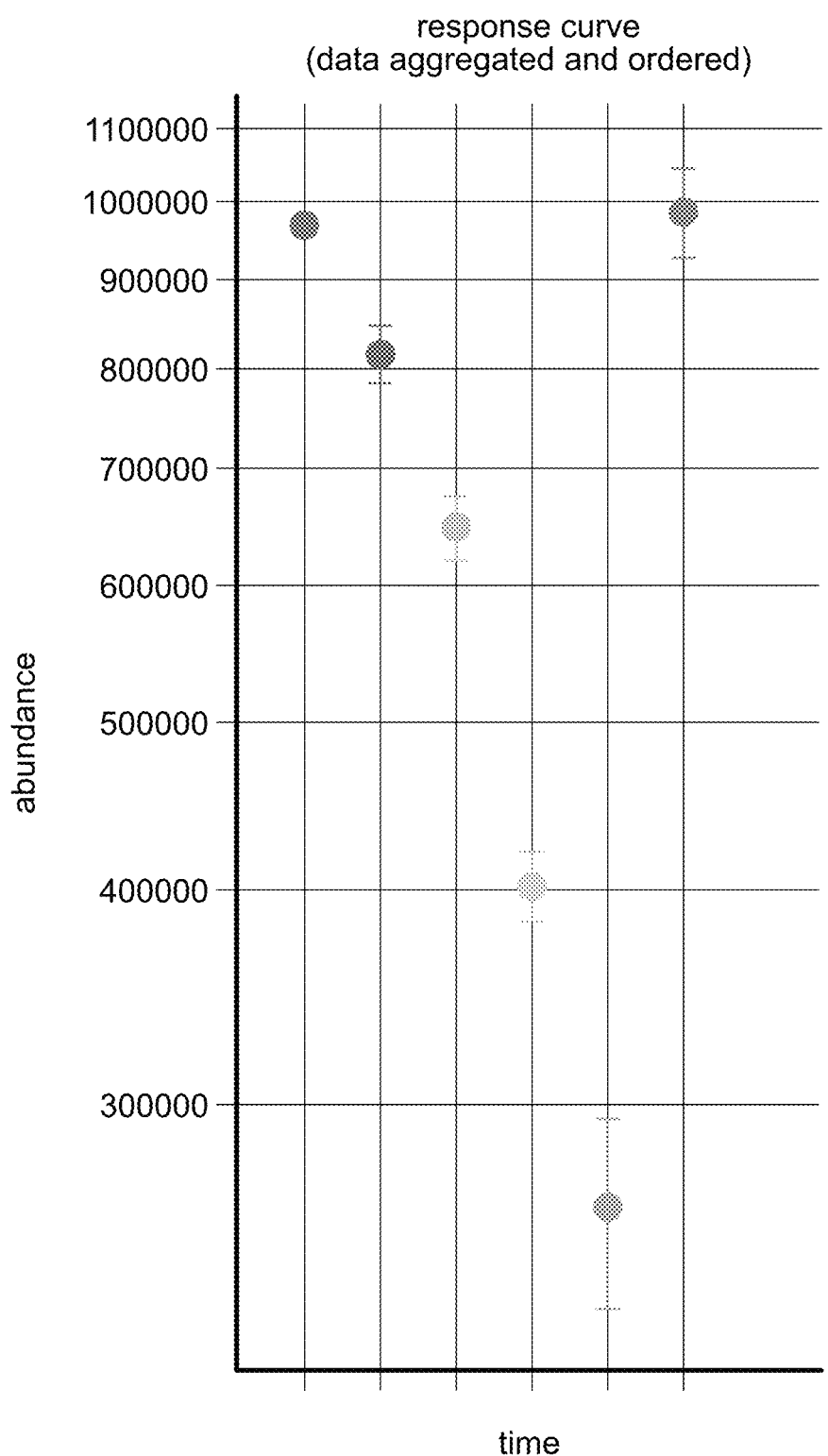

In various embodiments, consensus library may generate consensus libraries 225 for the matrix (or matrices) associated with matrix data 210a-n. In some embodiments, a consensus library 225 may include component characteristics for native components of the matrix, such as known-identified components and known-unidentified components (see, for example, libraries of common unknowns in human microsome examples in FIG. 5 and an illustrative consensus library in FIG. 10). In some embodiments, various information, including metadata, digital identifiers, and/or the like may be included in a consensus library and/or stored and related to a consensus library. See, for example, digital identifiers for a consensus library in FIGS. 4 and 7. In exemplary embodiments, the component characteristics may include an entry for each known component in the matrix (or each known-unidentified component) and associated component characteristics, including, without limitation, spectral data, m/z, retention time, drift time, CCS, incidence rate, neutral mass, monoisotopic mass, associated structures, product ion component characteristics (for instance, mass, m/z, and/or the like), fragments, fragment component characteristics, and/or the like. Embodiments are not limited in this context as consensus libraries 225 may include any type of detectable and/or calculated data associated with a component and/or fragments thereof.

Non-limiting examples of component characteristics used to evaluate matrix data 210a-n generate consensus libraries 225 may include m/z, retention time, drift time, CCS, mass, product ions, fragment ions, combinations thereof, and/or the like. For example, a consensus library 225 may be generated based on m/z; m/z and retention time; m/z, retention time, and CCS; m/z, retention time, product ions, and CCS; m/z and drift time; m/z, drift time, and retention time; m/z, drift time, and CCS; m/z, drift time, product ions, and CCS; m/z and CCS; m/z, CCS, and product ions, combinations thereof, and/or the like.

In various embodiments, selection of a component for inclusion in a consensus library 225 may be based on whether a potential component is over a threshold for one or more component characteristics of interest and/or incident rates (otherwise, in some embodiments, a potential component below such a threshold may be determined to be background noise). For example, a threshold for an m/z characteristic may be based on, among other things, mass accuracy (ppm). In another example, a threshold may include a minimum incident rate for the potential component over a plurality of analyses to be included in a consensus library 225. In a further example, a threshold may include a minimum concentration within the matrix to be included in the consensus library. Embodiments are not limited in this regard.

As shown in FIG. 2, flow B may include analytical instrument application 215 receiving sample data 240. For example, sample data 240 may include data generated as a result of an analysis of a sample associated with a particular matrix. For example, the analysis may include LC-MS analysis of a particular groundwater sample as part of a contamination analysis for pesticides in which the matrix is groundwater (for instance, a general groundwater matrix or a specific matrix previously determined for an area of interest, such as a body of water, municipal water supply, and/or the like). Sample data 240 may be processed by analytical instrument application 215 according to some embodiments and provided to consensus library logic 220. In various embodiments, consensus library logic 220 may compare sample data to a corresponding consensus library 225 (for instance, one or more groundwater consensus libraries) to determine non-native or unknown-unidentified components 245 in sample data 240. In exemplary embodiments, known-unidentified components (and, in addition, known-identified components) may be identified and/or removed from sample data such that the remaining data is only sample unknown-unidentified data 245. The unknown-unidentified data 245 may then be subject to further analysis, processing, and/or the like according to conventional techniques to identify the unknown-unidentified components of sample data to generate identified sample components 250.

Figure 3:
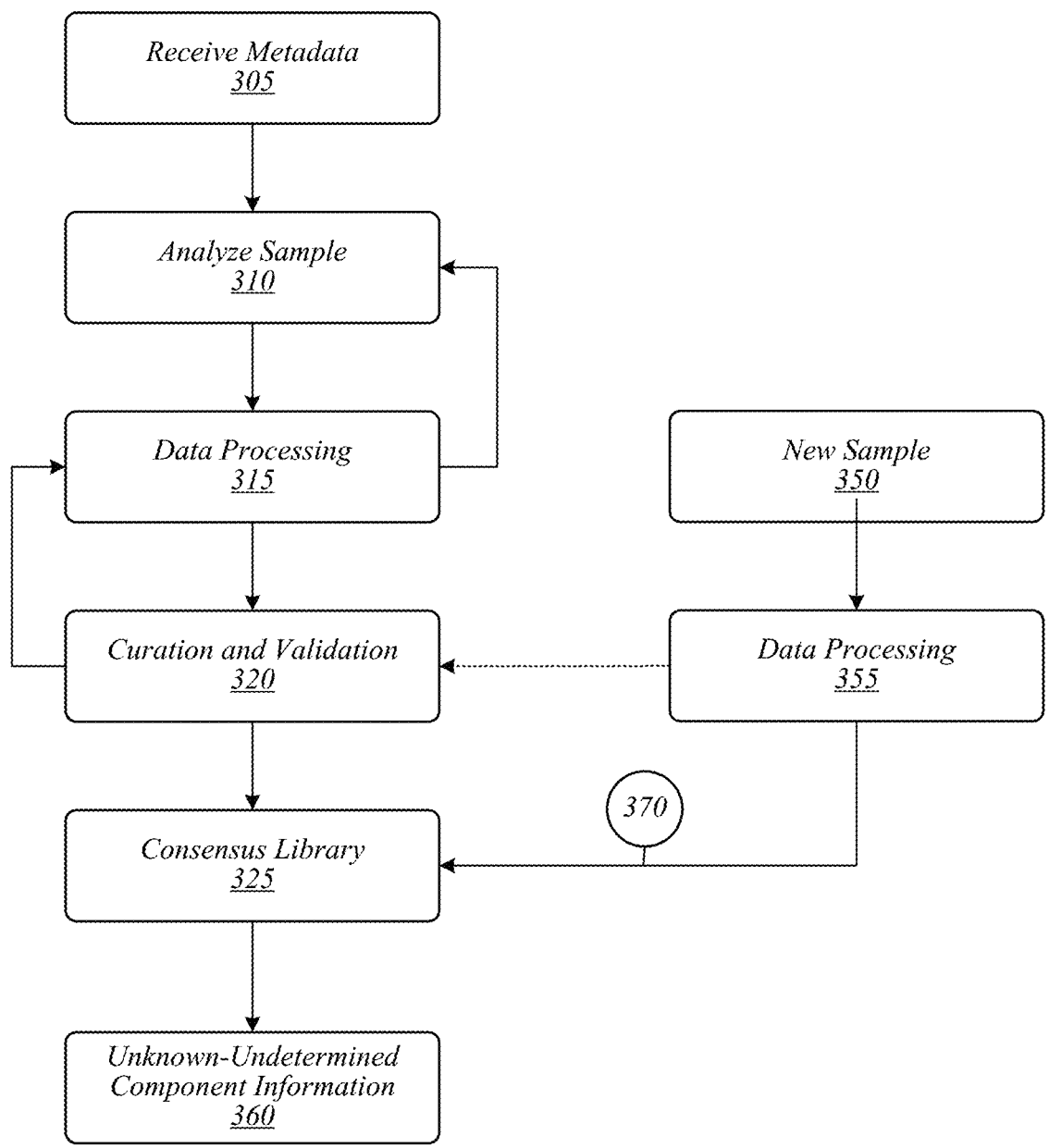
FIG. 3 illustrates an embodiment of a second logic flow according to some embodiments.

FIG. 3 illustrates an embodiment of a logic flow 300. Logic flow 300 may be representative of some or all of the operations executed by one or more embodiments described herein, such as analysis system 105 and/or computing device 110. For example, in some embodiments, blocks 305-325 of logic flow 300 may be representative of some or all of the operations of generating a consensus library. In another example, in some embodiments, blocks 325 and 350-360 of logic flow 300 may be representative of some or all of the operations of determining unknown-unidentified components of a sample using a consensus library.

At block 305, logic flow 300 may determine and/or receive metadata associated with a sample. In various embodiments, metadata may include any type of information associated with the sample and or analysis thereof, including, without limitation, sample identifiers, matrix information, analysis methods, instrument information, experimental procedures, data annotations, information relating an experimental design to produced data, and/or the like. Embodiments are not limited in this context. At block 310, the sample may be analyzed (or data from an analyzed sample may be received) by logic flow 300. For example, at block 310, logic flow may receive or determine componentized data (for instance, information associated with the components of the sample). Logic flow 300 may process the sample information may be according to some embodiments (for example, via analytical instrument application 132) at block 320. Logic flow 300 may perform curation and/or validation at block 325 to generate a consensus library for the sample at block 330. In some embodiments, curation and/or validation may include automated curation and/or validation processes. In various embodiments, curation and/or validaton may include manual curation and/or validation processes. In general, in various embodiments, curation and/or validation may include correcting values (for instance, compound characteristic values such as m/z, CCS, and/or the like), removing unwanted fragment ions, and/or the like. In general, curation and/or validation may include processes to ensure high-quality and accurate data that removes, for example, system artifacts, background noise, and/or the like. At block 325, logic flow 300 may generate a consensus library for the matrix associated with the sample according to some embodiments. The consensus library may include known-unidentified components of the sample matrix.

At block 350, logic flow 300 may analyze (or receive analysis information of) a new sample associated with the matrix of consensus library. The analysis information for the sample may be processed according to some embodiments at block 355. As shown in FIG. 3, information resulting from data processing at block 355 may be provided to block 320 for curation and validation and the information used to update the consensus library for the matrix at block 325. In this manner, each new sample relating to a matrix may be used to update, curate, teach, improve, or otherwise adjust the consensus library. For example, new samples may modify the population of known-unidentified components of the consensus library and/or component characteristics of the components. Logic flow 300 may process the information of the new sample using a consensus library 370 at block 325 to generate unknown-unidentified component information associated with the new sample at block 360.

Figure 8:
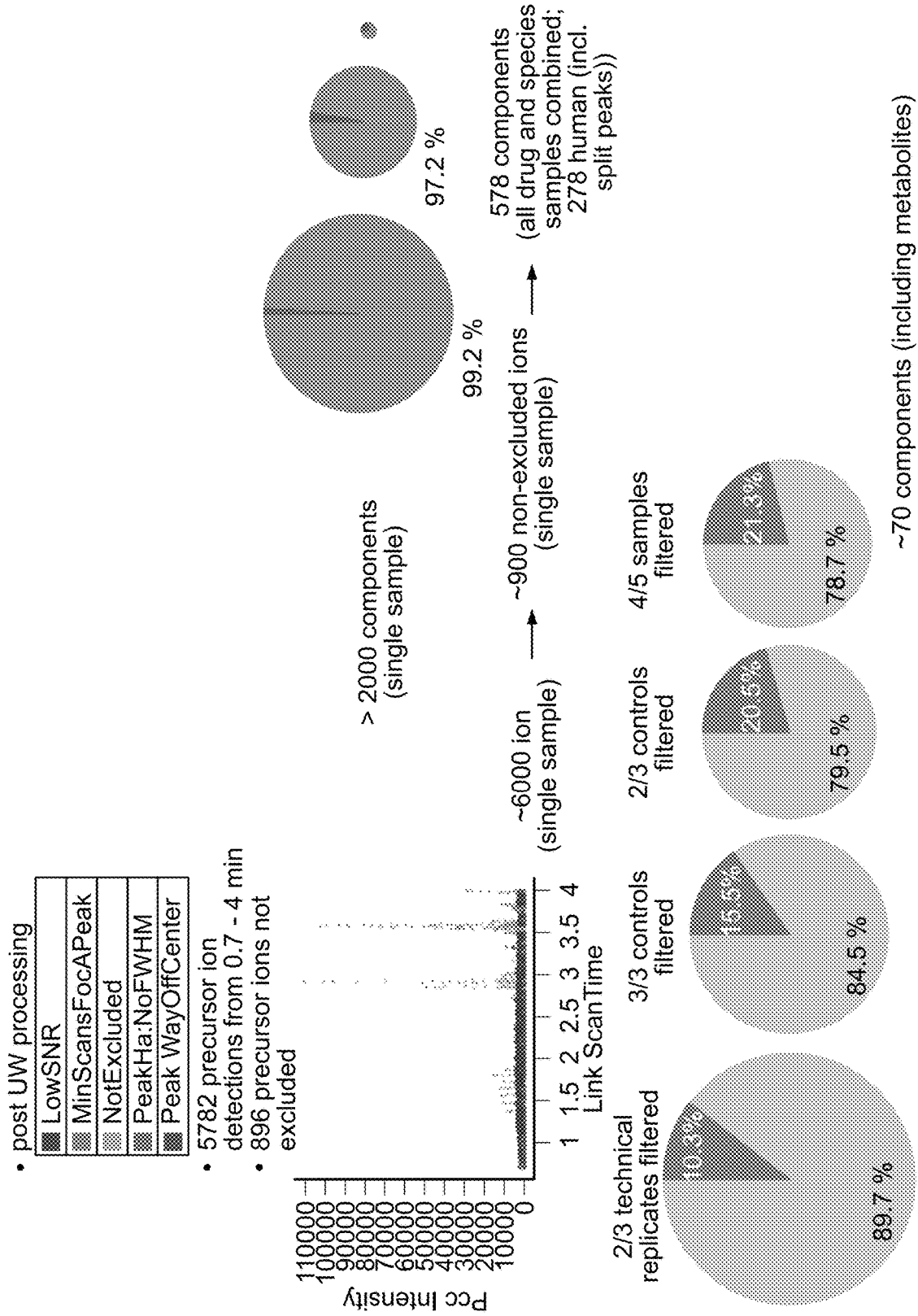
FIG. 8 illustrates graphical results of filtering a sample using a consensus library according to some embodiments.

In various embodiments, a consensus library may include a total body of components present in a sample matrix that may be excluded to focus characterization of a sample on unknown components resulting from the experiment. In comparison to a conventional binary compare approach, processes according to some embodiments which use consensus library-based process result in a significantly greater enrichment rate (n[true positives]/n[total components]). Accordingly, processes according to some embodiments represent more efficient and effective analysis processes, saving time and resources. FIG. 8 graphically represents the technological advantages of using consensus libraries for sample analysis according to some embodiments.

As shown in FIG. 8, initial analysis of a sample may result in a large number of components, such as greater than 2000 components. Consensus filtering using for example, but not limited to, technical replicates, controls, etc. may reduce the number of components, but still leads to a large number (for example, about 1000 or greater). However, use of a consensus library according to some embodiments may decrease the number of unknown components to a much smaller number, such as about 70 as depicted in FIG. 8. Here, a conventional binary comparison will typically fail. Accordingly, use of consensus libraries according to some embodiments provides for a much more efficient and accurate process, for example, at least in terms of reducing false discovery rates, for determining the composition of a sample compared with conventional processes.

EXPERIMENTS

Experiment I: Generation and Use of Hepatocyte Consensus Library

Human hepatocytes incubations were subjected to protein precipitation, centrifuged, and the supernatant collected for LC-MS analysis. Ion mobility enabled data independent acquisition (HDMSE) LC-MS data were acquired with two different reversed phase gradient methods using an ACQUITY I-class system and a VION IMS QTOF Mass Spectrometer manufactured by Waters Corporation of Milford, Massachusetts, United States of America. Multi-dimensional precursor and product ion peak detection was conducted with UNIFI™ software and the data analyzed with library building tools configured according to some embodiments. Briefly, the data were co-detected across all samples in the m/z and retention time dimensions and validated by CCS. An aggregate peak list was constructed from which an initial query consensus library was developed. Through an iterative search and (Kendrick) filtering process, the content of the consensus library was curated and appropriate query parameters derived Five technical replicate LC-MS experiments of two independent incubations were conducted per gradient method. Four of the five replicates were used for consensus library creation and the remaining replicate for testing and evaluation. The initial consensus library included components that were consistently detected across all runs with regard to m/z, retention time, and drift time reproducibility. No restrictions were applied at this stage with respect to intensity and/or number of fragment ions. Appropriate search tolerances were readily obtained by considering every possible match parameter, resulting in a set of parameters that are equivalent to those typically applied in studies were the structure and/or elemental composition of the target molecules are known. The curation process provided for the estimation of the contribution of each analytical parameter, either individually or combined, to the overall specificity of a compound search. In addition, two methods were considered and evaluated that express normalized specificity metrics either as a function of the number of detections or curated library entries, respectively. The application of the consensus (or "known-unknown") library and the ability to estimate false discovery rate was achieved via hepatocytes incubation matrices spiked with known reference compounds and metabolites.

Figure 9:
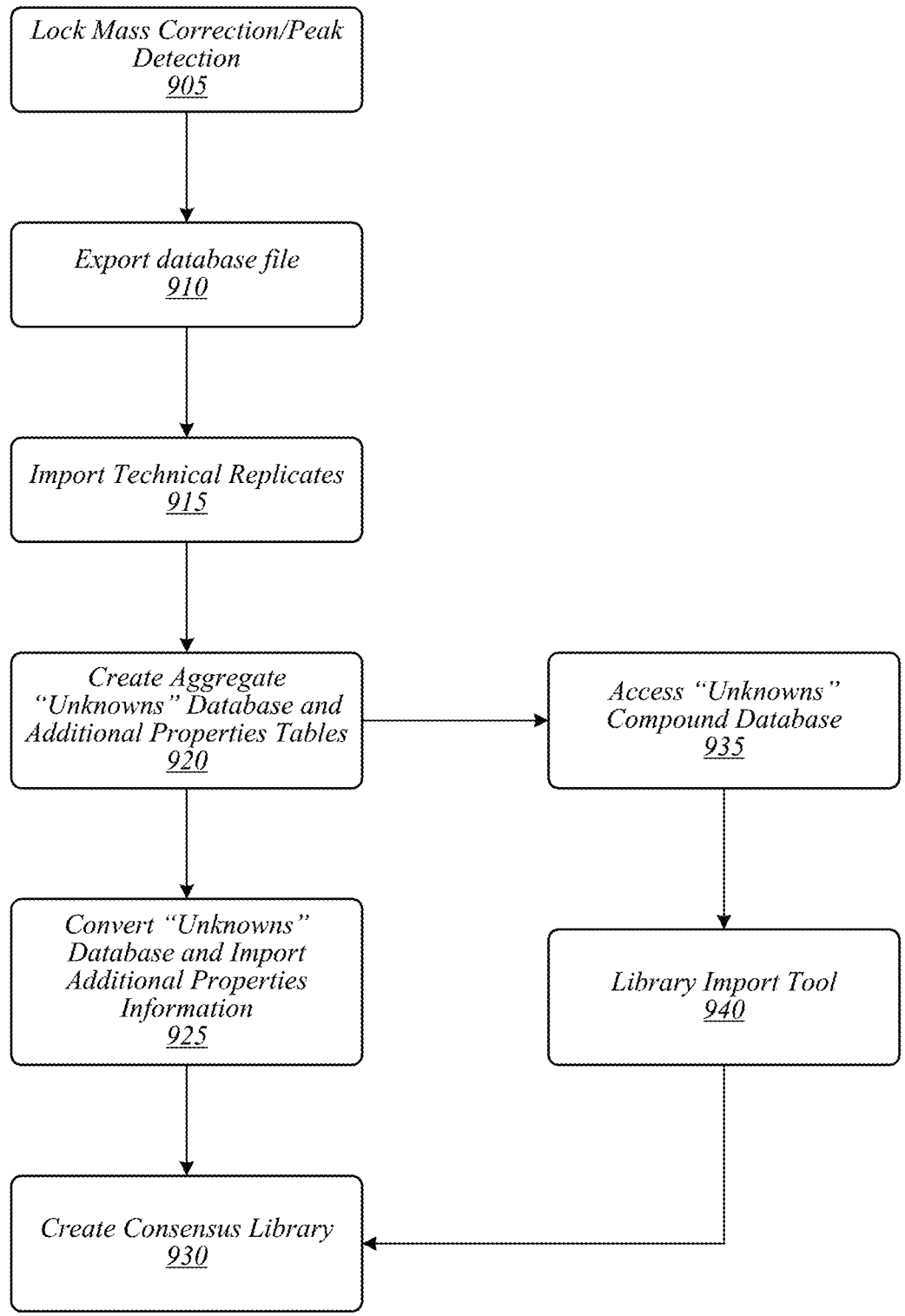
FIGS. 9-14 illustrate results of a first experiment performed according to some embodiments.

FIG. 9 depicts an illustrative logic flow for generating a consensus library according to some embodiments in Experiment I. As shown in FIG. 1, logic flow 900 may start by locking mass correction/peak detection at block 905, exporting database files at block 905 and importing technical replicate at block 915. At block 920, logic flow 900 may create an aggregate "unknowns" database (for instance, *.msp file) and additional properties (for instance, retention time and/or CCS) tables. Logic flow 900 may convert (for instance, transpose) "unknowns" database (for instance, *.msp to *.csv or *.xls or equivalent format) and import additional properties (for instance, CCS and/or retention time) information at block 925 and create a consensus library at block 930. At block 935, logic flow 900 may access "unknowns" compound database (for example, Progenesis™ QI "unknowns" database) and use a library import tool 940 (for instance, a UNIFI™-based scientific library import tool that, for example, accepts neutral masses without structures and formulas) for input for creating a consensus library at block 930.

In Experiment I, creating a consensus library may include a first step in which: UNIFI™ *.uep files may be created and imported into Progenesis™ QI (for instance, Progenesis QI); default import settings were used with the exception of detection threshold (for instance, 0 intensity); 8/10 sample files were imported (4/sample type ('matrix') and co-detected) and sample files were placed into two groups ('matrix01' vs. 'matrix02'); detections were retained only if fragment ions were associated with a feature; detection results were exported, replicating ('8/8') features retained and tag list based on identifier (compound) was generated; a filtered feature list was imported and results tagged based on filtered list and results filtered to '8/8' tag; and replicating fragment ion spectra exported as an *.msp file.

In Experiment I, creating a consensus library may include a second step in which: the *.msp file was converted to a *.csv file; neutral m/z values were calculated and appended to the column(s); and CCS values and retention times were appended to the *.csv file (or "spread sheet") (for instance, from Progenesis QI detection result export function).

In Experiment I, creating a consensus library may include a third step in which: a library file (for instance, an *.ucl file) is generated from the spread sheet file, for example, using a UNIFI™ tool that accepts neutral m/z values instead of elemental composition as the identifier.

Figure 10:
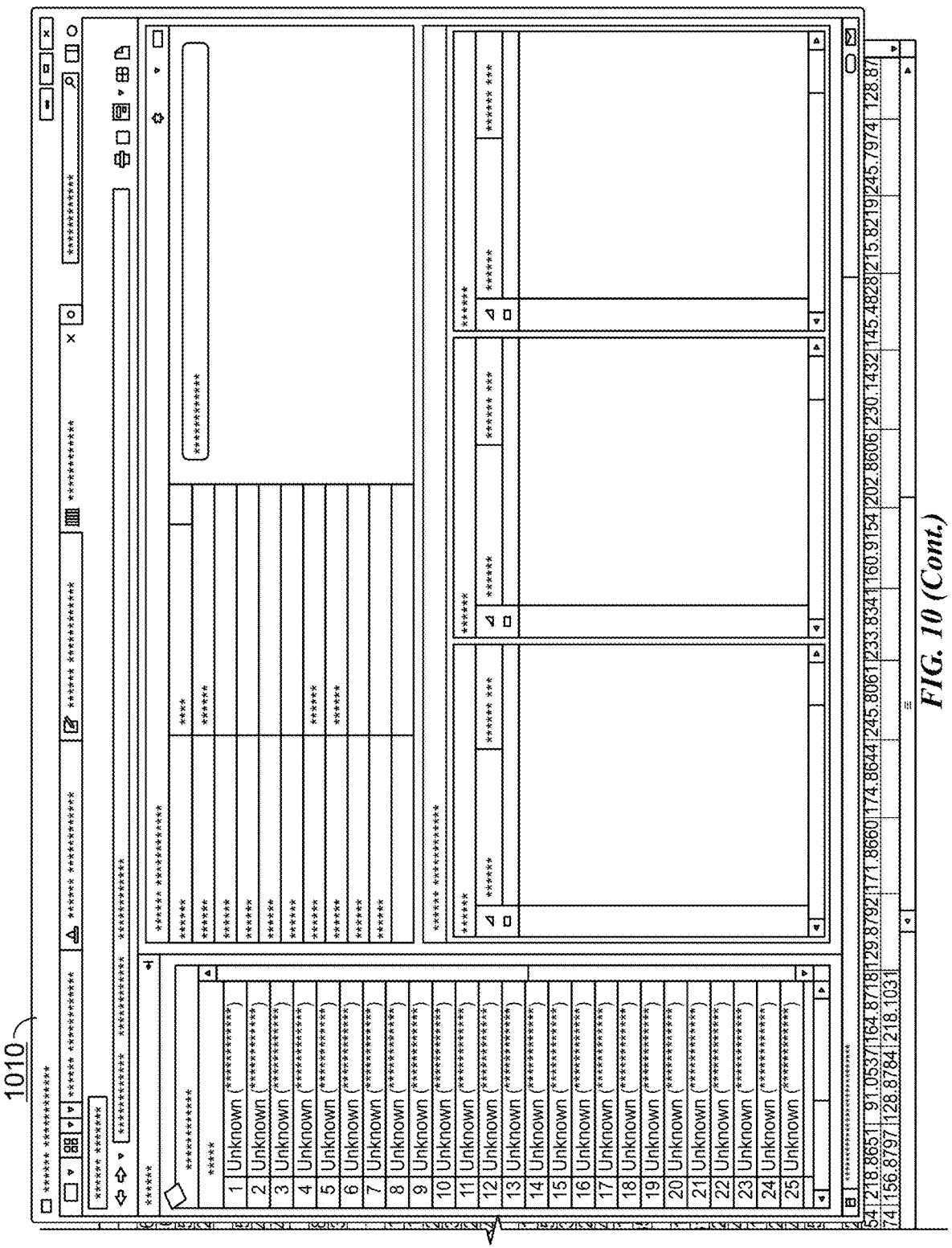

FIG. 10 depicts an illustrative consensus library file 1005 generated according to some embodiments in Experiment I and a component interface 1010 providing information for a component of consensus library file 1005.

Sample files not used for consensus library creation were used to search against the consensus library to detect known-unidentified components and to estimate the variance of the data sets in the various domains of interest (for example, m/z, CCS, and/or retention time). In Experiment I, the number of product ions per library entry was not restricted. The criteria and parameter combinations in Table 1 were utilized in Experiment I:

TABLE 1

| Pass 1 Criteria (Case 0) | Parameter Combinations |
| --- | --- |
| m/z ± 15 ppm | m/z |
| $t_r$ ± 1 min | m/z and $t_r$ |
| CCS ± 10% | m/z and CCS |
| | m/z, CCS and $t_r$ |
| | m/z, CCS and MS/MS |
| | m/z, CCS, MS/MS and $t_r$ |

Figure 11:
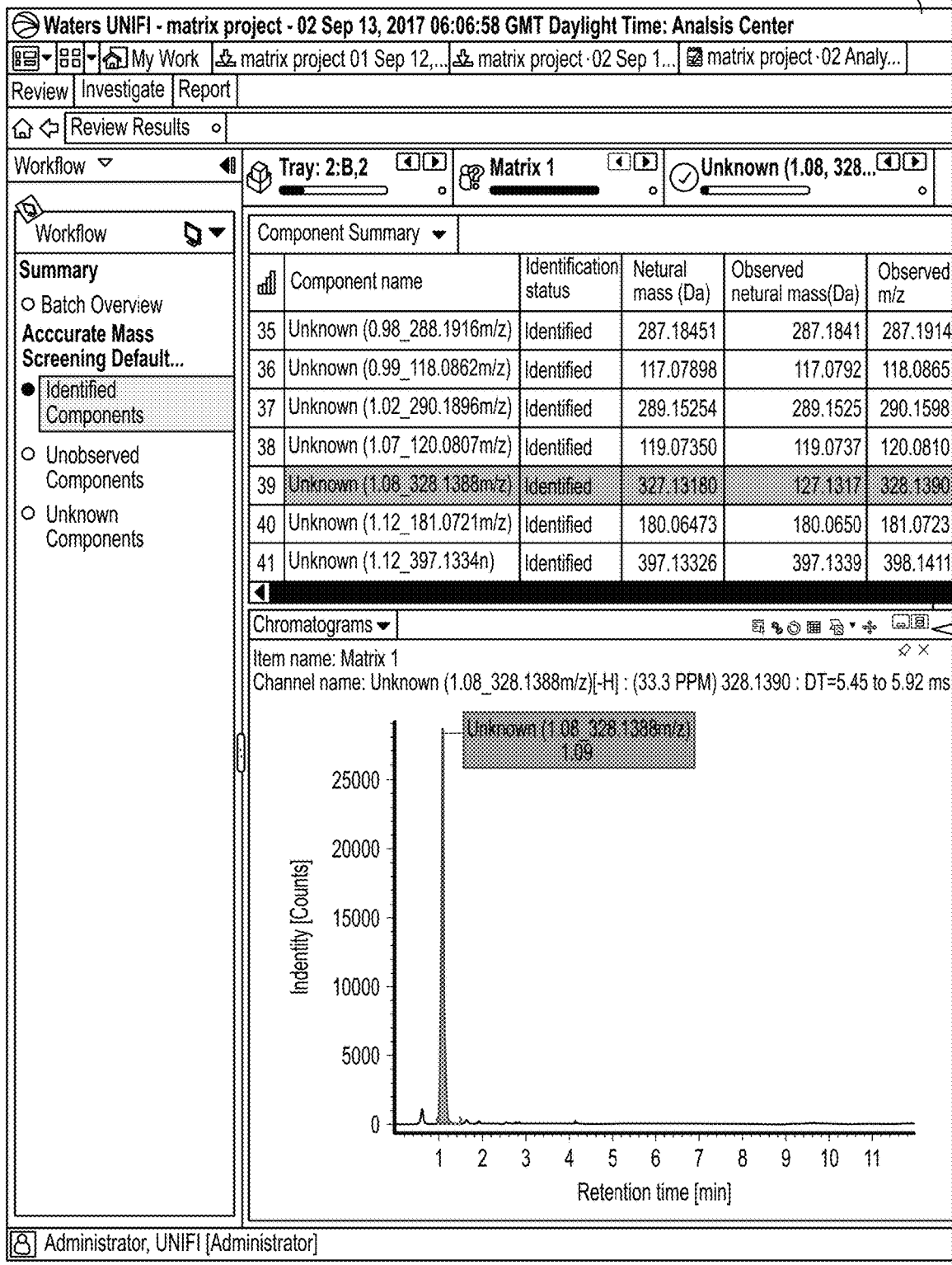
Figure 11:
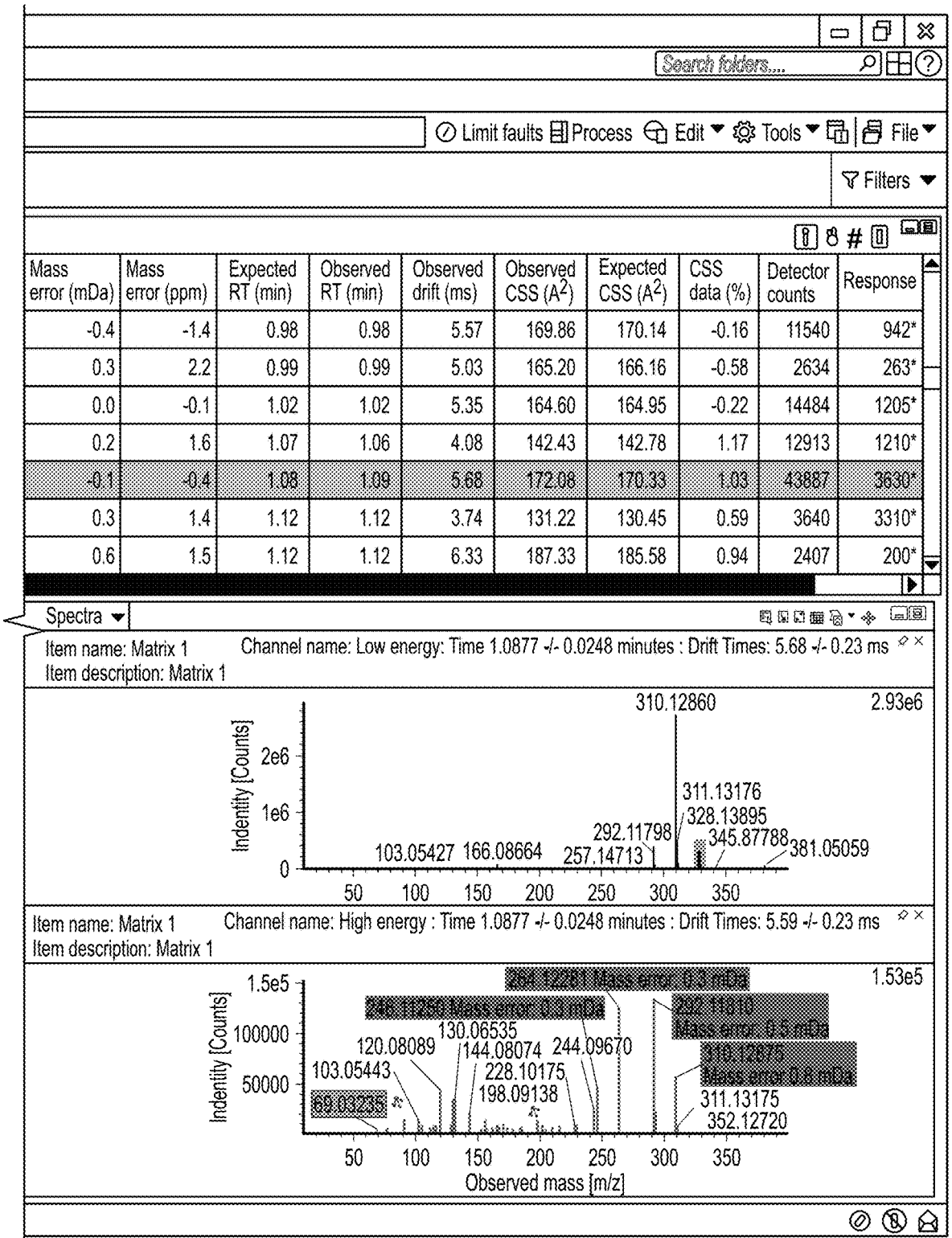
Figure 12:
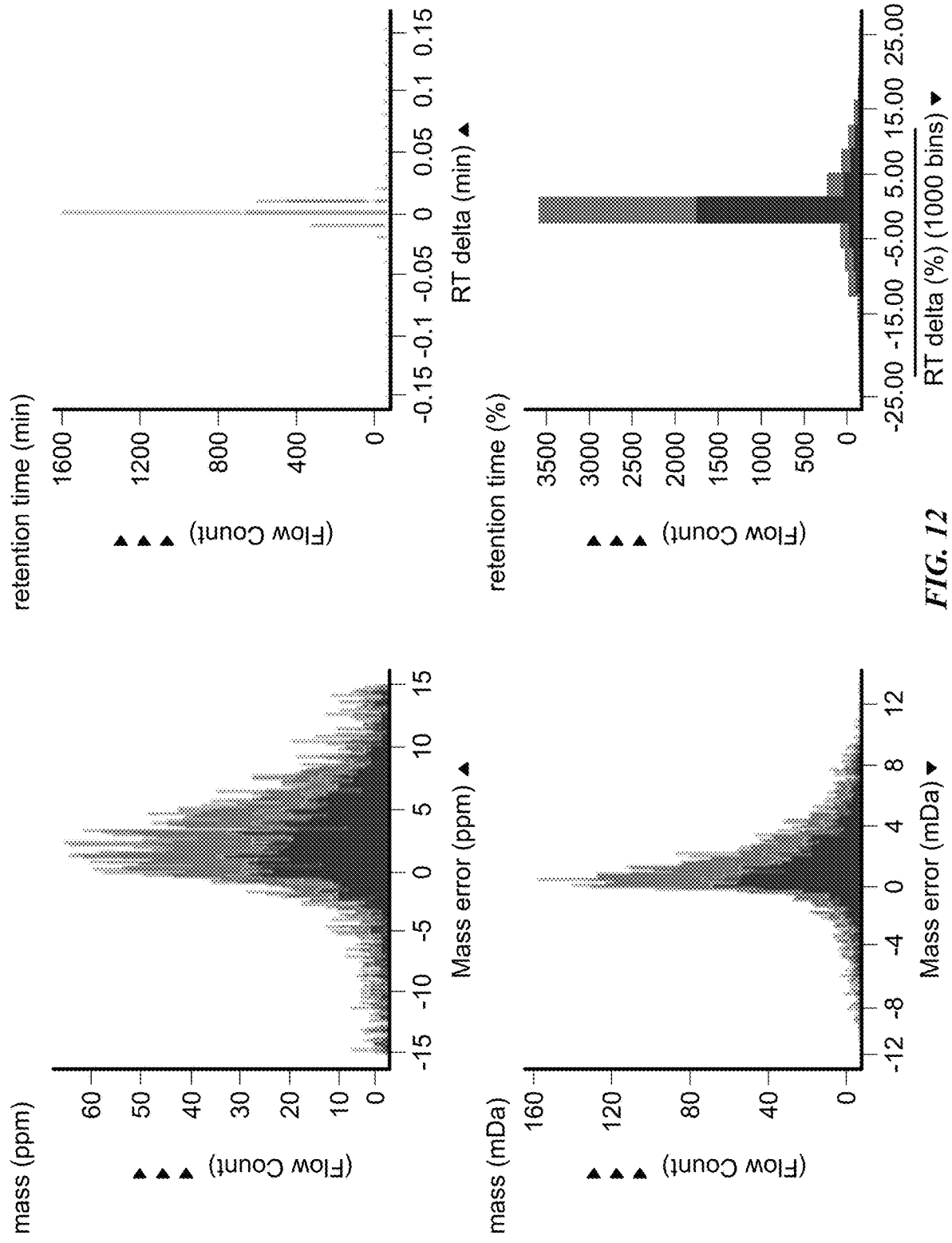
Figure 12:
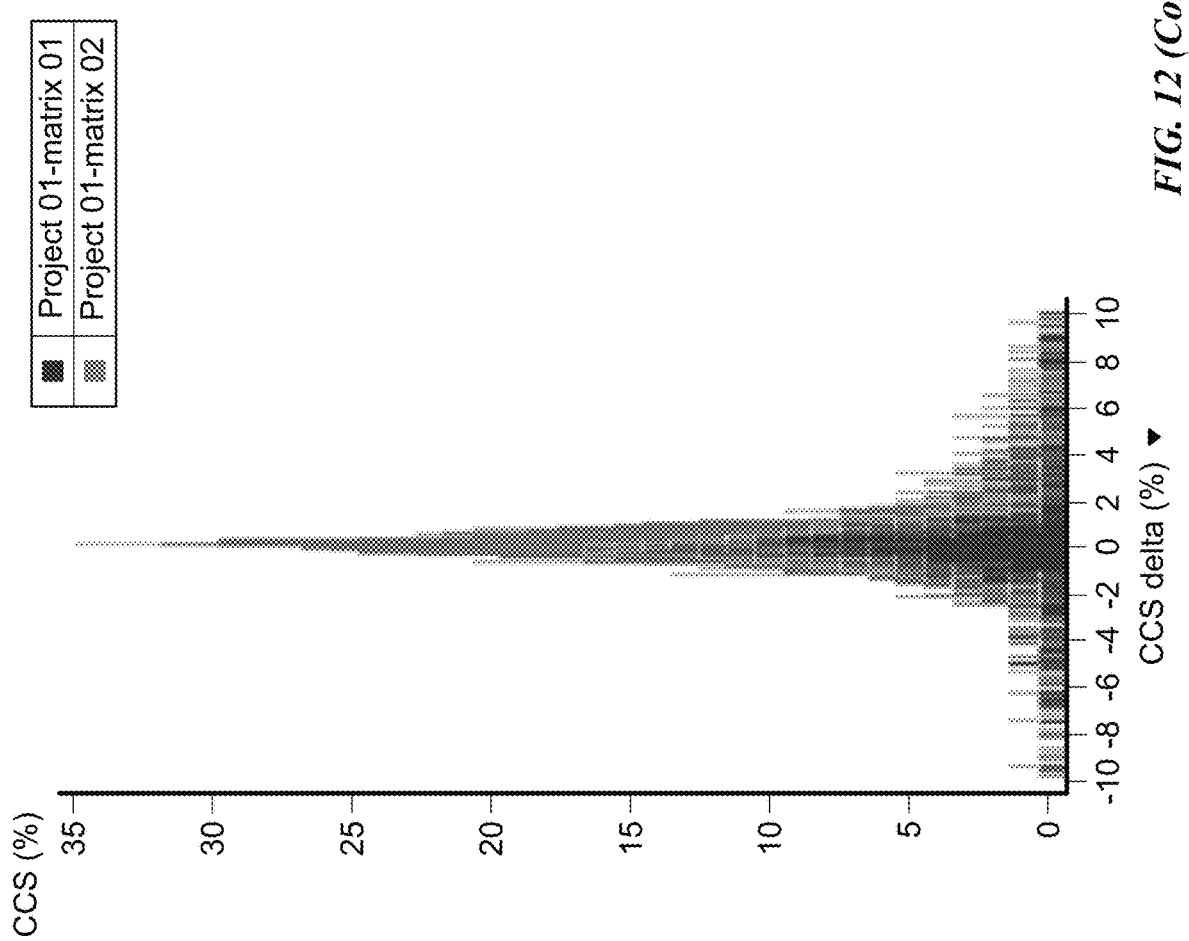

FIGS. 11 and 12 depict identification examples within the UNIFI™ platform. Table 2 provides standard deviations for parameter combinations/cases of 0 (least selective) to 6 (most selective):

TABLE 2

| Parameter | (0) | (6) |
| --- | --- | --- |
| m/z (ppm) | 5.2 | 3.8 |
| $t_r$ (min) | 0.3 | 0.2 |
| CCS (%) | 2.0 | 1.1 |

In some embodiments, case (6) standard deviations may be used as the search/match criteria to reduce unintentional false identifications (for instance, increasing false discovery rate (FDR) values).

Figure 13:
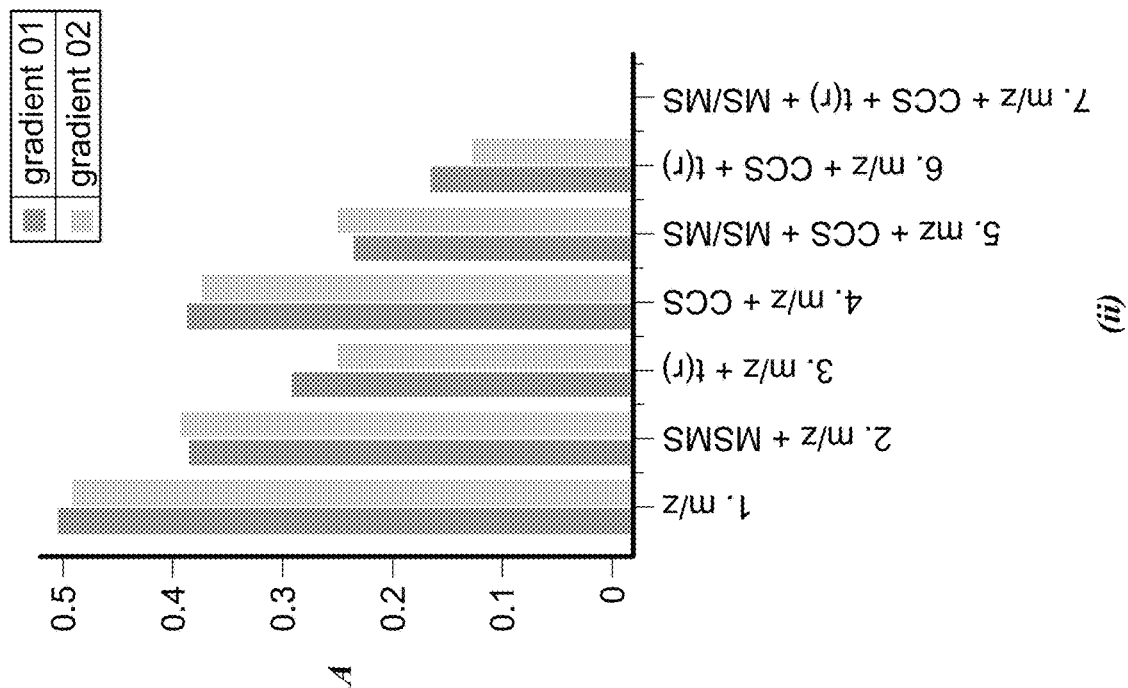
Figure 13:
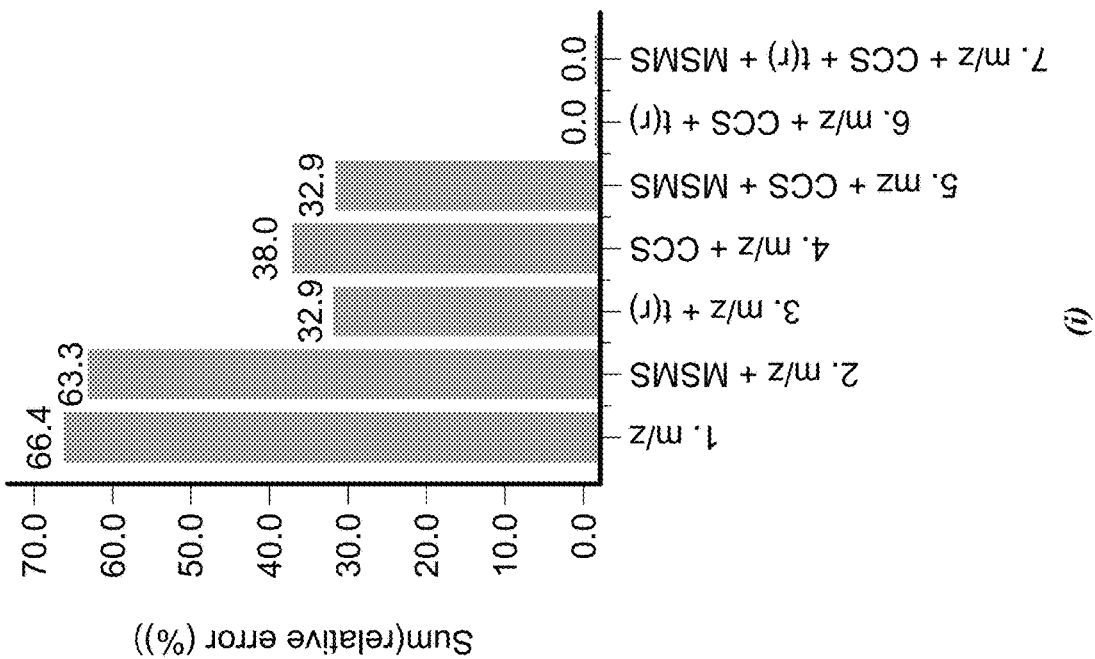
Figure 14:
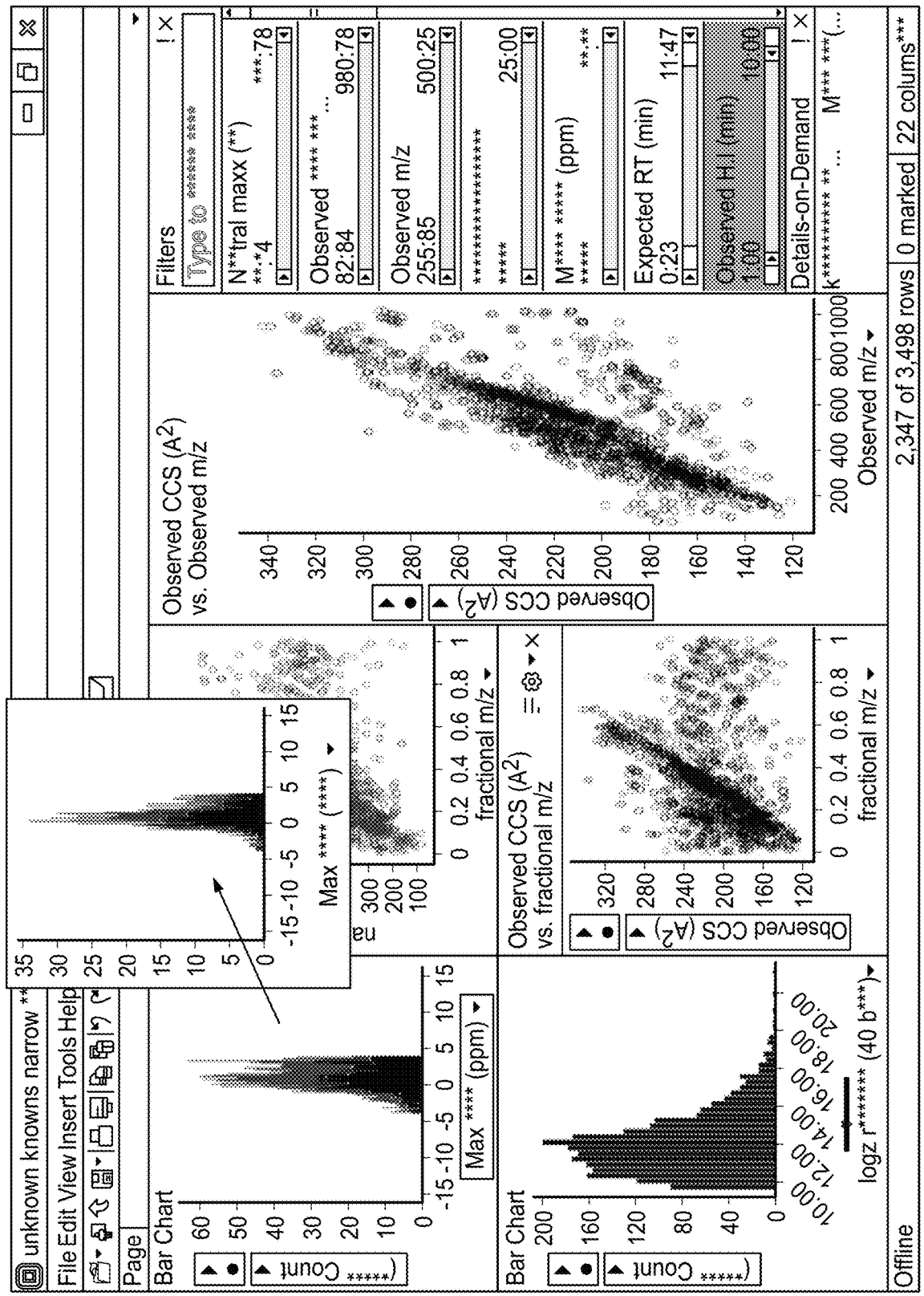

In Experiment I, the queries for the 6 cases were repeated with following tolerances and a seventh case (m/z+MS/MS) included: Criteria (1) m/z±3.8 ppm, (2) $t_r$±0.2 min, and (3) CCS±1.1%. Two measures of 'incorrectness' were considered: (i) normalize the number of detections that reside within the search space when all parameters (for instance, m/z, $t_r$, CCS and MS/MS) would have been considered over the number of detected known-unidentified compounds (or "known-unknowns") for a given (set of) parameters, and subtracting this value from 1, and (ii) a variant where the number of detected known-unidentified compounds (or "known-unknowns") was normalized over the number of library entries first, followed by normalization over the number detections considering all parameters (for instance, m/z, $t_r$, CCS and MS/MS), and the resulted number subtracted from 1 as well. In some embodiments, the closer the value to zero (or zero %), the more specific a search is expected to be. FIG. 13 depicts the cases for (i) and (ii). The contribution to assay specificity of any of the parameters compared to any other (combination of) parameters may be estimated by calculating a ratio value of the individual values calculated for case ii. FIG. 14 depicts search results showing clockwise, m/z (ppm) error distribution, nominal m/z vs. residual m/z, CCS vs. m/z, CCS vs. residual m/z, and log 2 MS1 (HDMSE) ion intensity distribution.

In Experiment I, for all parameters/dimensions, the distributions center around zero; however, the apparent m/z distributions were high m/z skewed. The greatest contributing parameter to the skew was intensity and to a smaller degree mass defect; however, a relatively larger portion of the low abundant ions were found to be more biased towards high residual m/z values.

In some embodiments, restricting the number of product ions per library compound (for example, to a maximum of five) may reduce the m/z skew marginally but had a significant effect on the absolute and relative number of identifications compared to a library that was not restricted on number of product ions per library compound. For example, using a library with a maximum of five product ions per library compound significantly reduces the number of possible detections.

Experiment II: Consensus Library for Drug Metabolism Applications

Figure 15:
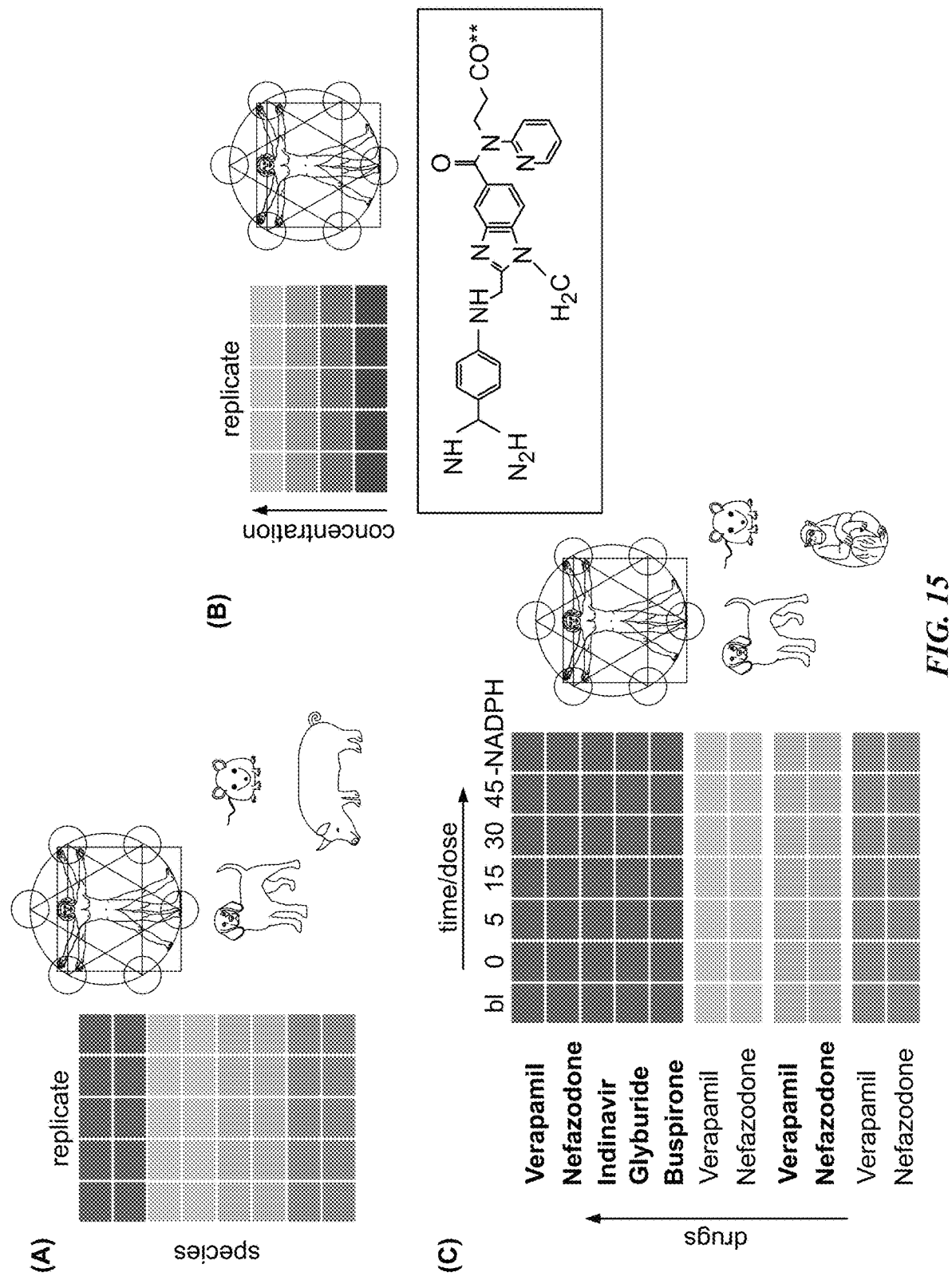
FIGS. 15-24 illustrate results of a second experiment performed according to some embodiments.

Five independent human, rat, dog, and mini pig hepatocytes matrices (1 M cells) were incubated for 6 hours. In addition, a separate human hepatocytes sample was spiked with a cocktail of metabolites at three concentration levels. Human, rat, dog, and monkey microsome matrices were incubated for 0, 5, 15, 30 and 45 min in the presence/absence of a variety of drug compounds and/or NADPH. FIG. 15 depicts experiments (A), (B), and (C) for Experiment II. Experiment (A) involves library characterization (human subset) and hepatocyte complement species comparison. Experiment (B) involves metabolite mixture spike for FDR estimation. Experiment (C) involves multi-species microsome aggregate spectra consensus library creation and validation.

Data were collected in positive ionization mode on Vion IMS Q-ToF and Synapt G2.Si platforms using ion mobility assisted data independent acquisition methods (HDMSE). Linear and non-linear reversed phase gradients were delivered with ACQUITY H-class systems and experimental (matrix preparation) and technical LC-MS replicate data collected.

The Vion IMS Q-ToF LC-MS data were peak (co-) detected and processed with versions of Progenesis™ QI and UNIFI™ software. Libraries, including retention time, CCS, m/z, and MS/MS information were created according to some embodiments.

Figure 16:
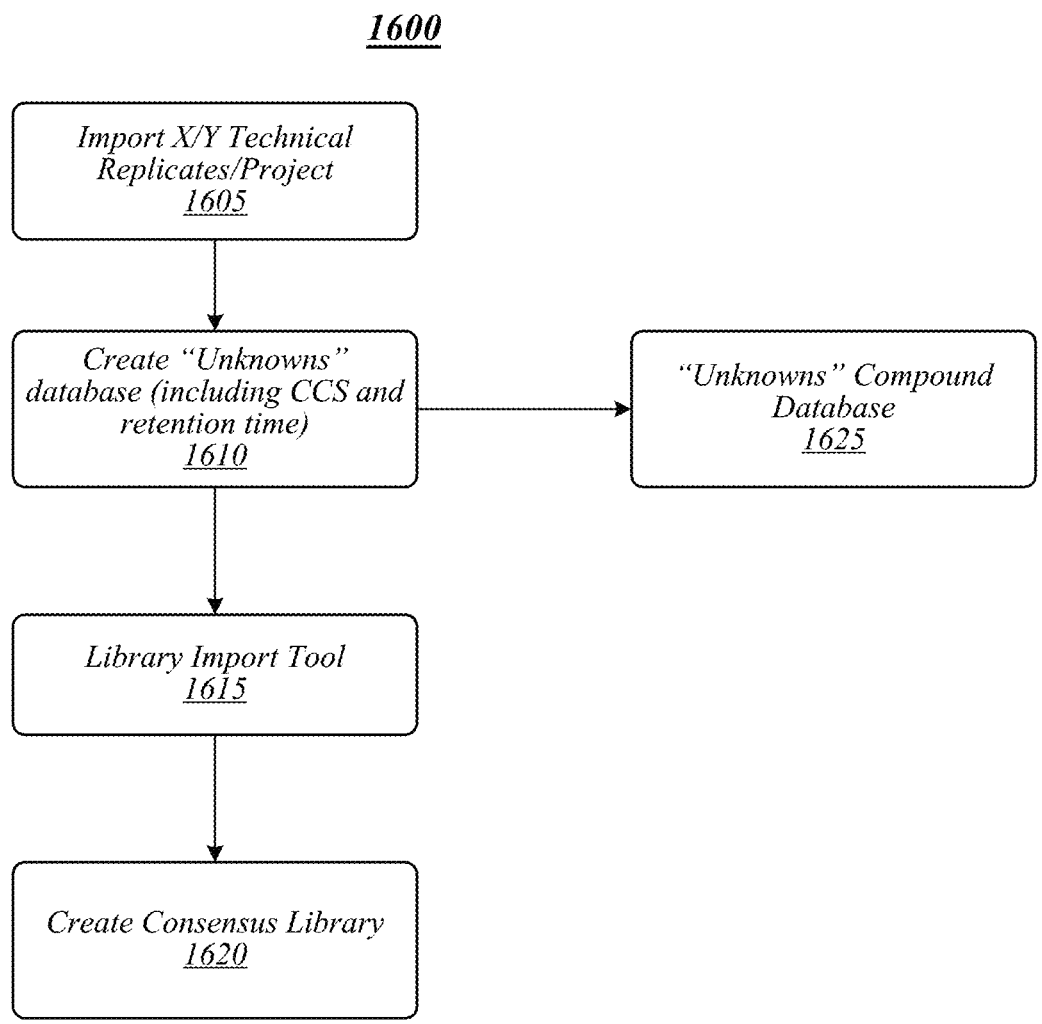

FIG. 16 depicts a consensus library creation logic flow according to some embodiments for Experiment II. As shown in FIG. 16, logic flow 1600 may import x/y technical replicates/project (Progenesis™ QI) at block 1005, create "unknowns" database (including CCS and retention time) at block 1610, initiate a library import tool at block 1615, create a consensus library at block 1620, and provide information from block 1610 to the "unknowns" compound database (for example, within Progenesis™ QI) at block 1625.

For library creation in Experiment II, the data were imported, aligned, and aggregated in Progenesis™ QI from which a consensus (or "native") library was derived according to some embodiments. The library was filtered on replication and number of fragment ions, converted and imported back into UNIFI™ (for example, at block 1515 of FIG. 15, using a tool that accepts neutral masses without structures and formulae). The number of diagnostic fragment ions was found to be m/z and precursor intensity dependent with a median value centering around 5 product ions per MS/MS spectrum and increases by 12 to 28% when applied as a metric/filter.

Experiment (A) was used to determine suitable search parameters. Four of the five replicates were used to create a matrix library according to some embodiments with the remaining replicate used to query the library. The following parameters were considered/evaluated and used as filters: (1) m/z, t(r), and CCS tolerances; (2) intensity and number of product ions; and (3) Kendrick mass defect.

Figure 17:
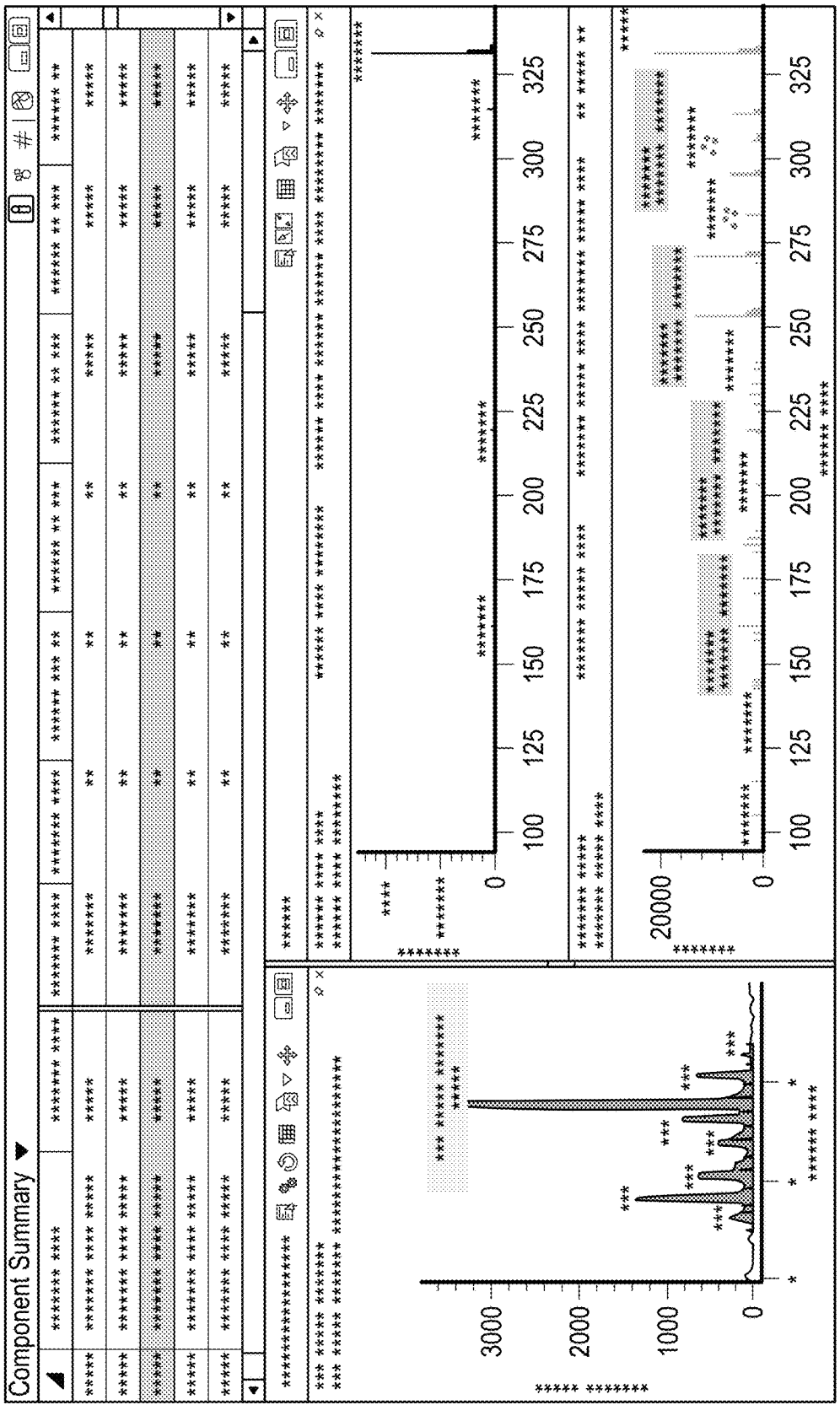

FIG. 17 depicts results generated in Experiment II. Panel 1705 depicts a detection example for a known-unidentified ("known-unknown"), panel 1710 depicts matrix replicate reproducibility, panel 1715 depicts tolerance estimation/error distribution of known-unidentified ("known-unknown") queries, and panel 1720 depicts m/z and CCS based known-unidentified mapping liner vs. non-linear gradient. As depicted in FIG. 17, are the distribution characteristics illustrating a high degree of replication/precision in all dimensions (for instance, in 1710 and 1715). A single standard deviation (a) was used as an unknowns search parameter tolerance, equaling ±3.8 ppm (m/z), ±1.1% (CCS), and ±0.2 min (t(r)) (panel 1115). Mapping/searching solely based on precursor m/z and CCS may provide estimation of the contribution of t(r) to the search specificity (panel 1720).

Figure 18:
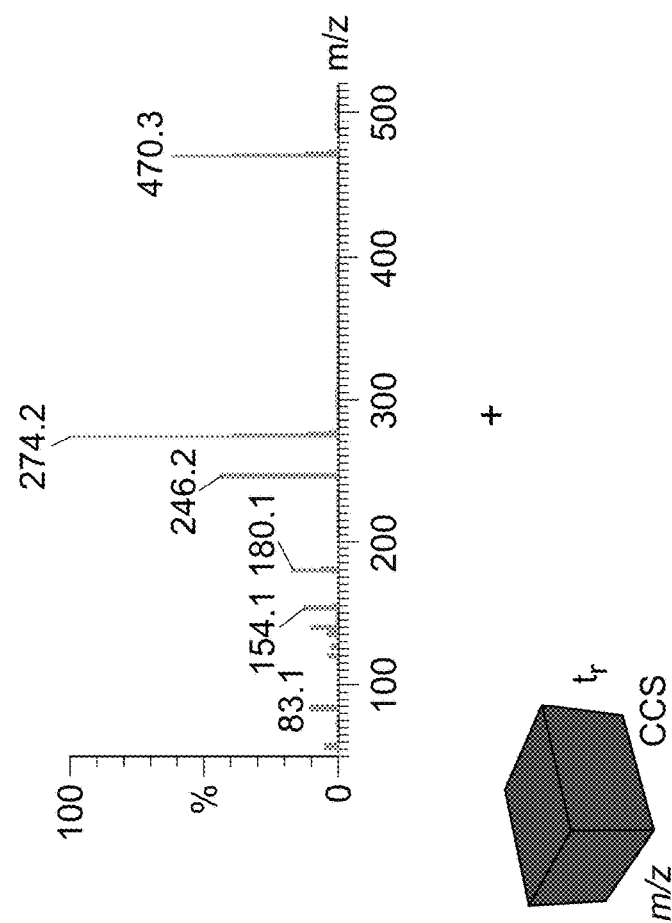
Figure 18:
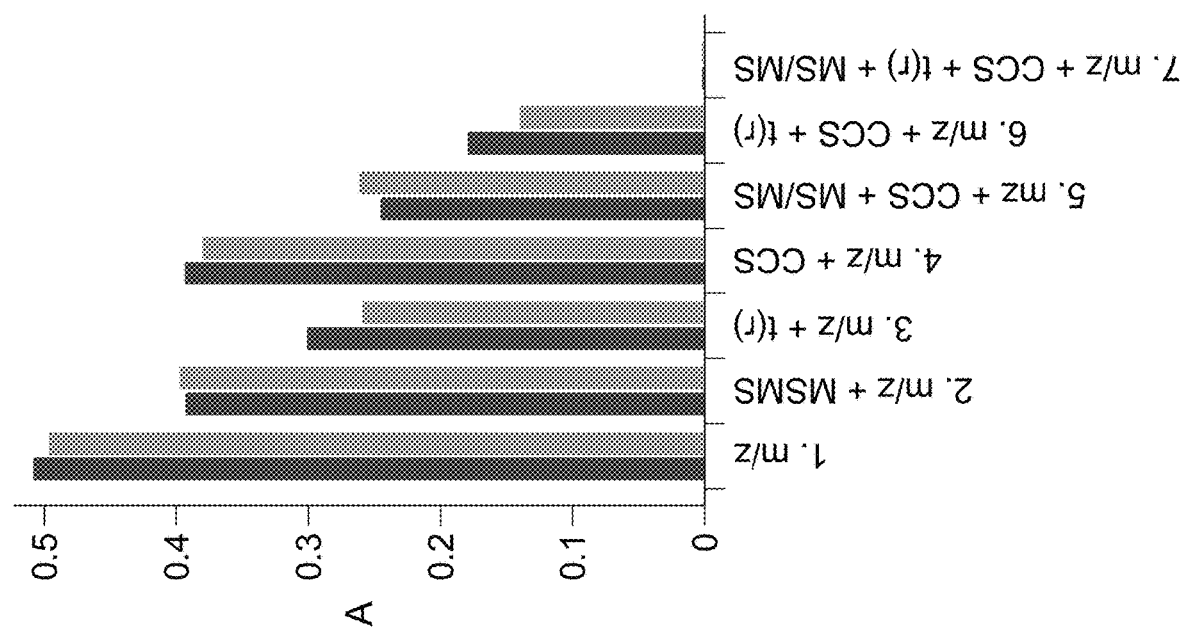
Figure 19:
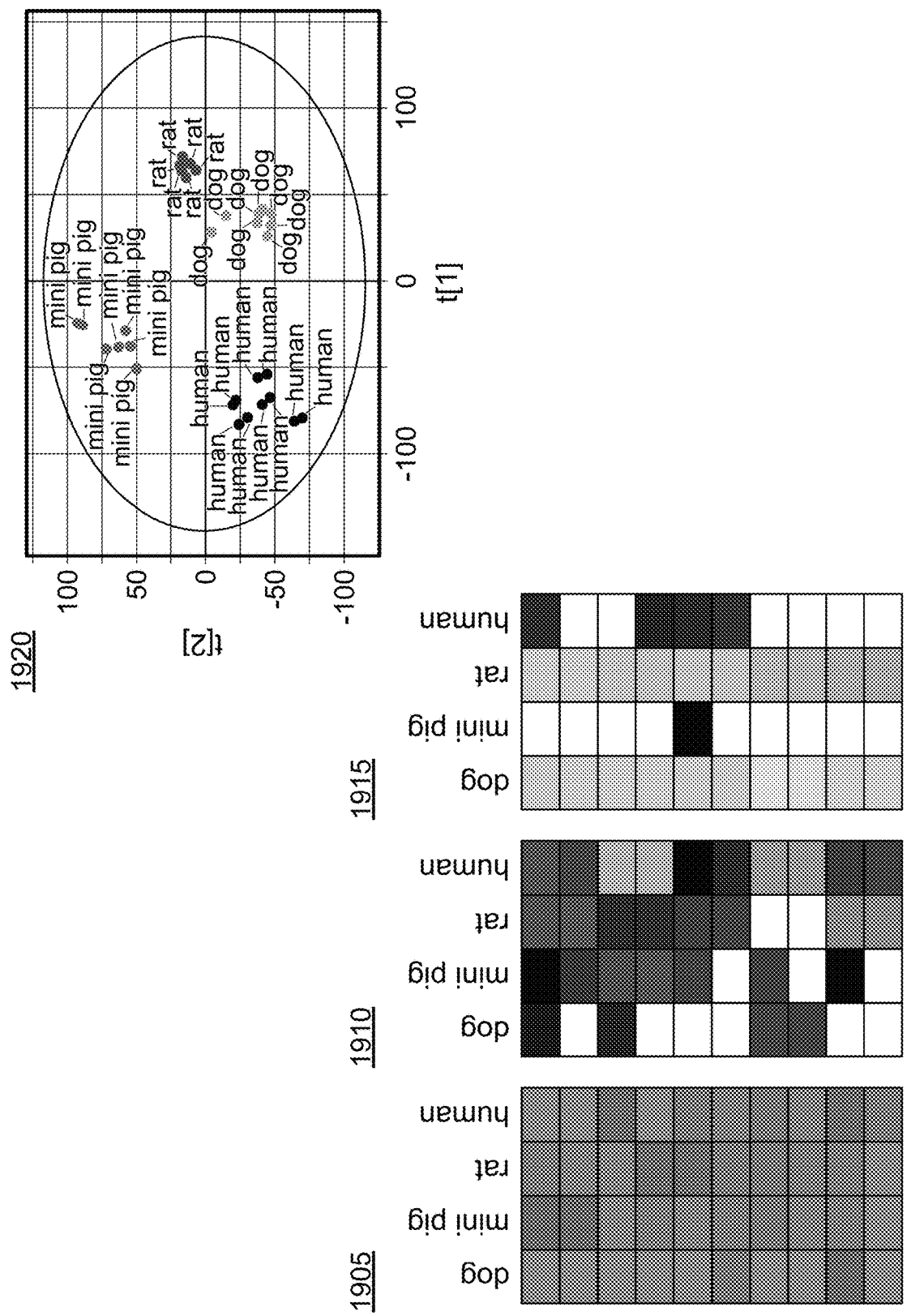
Figure 20:
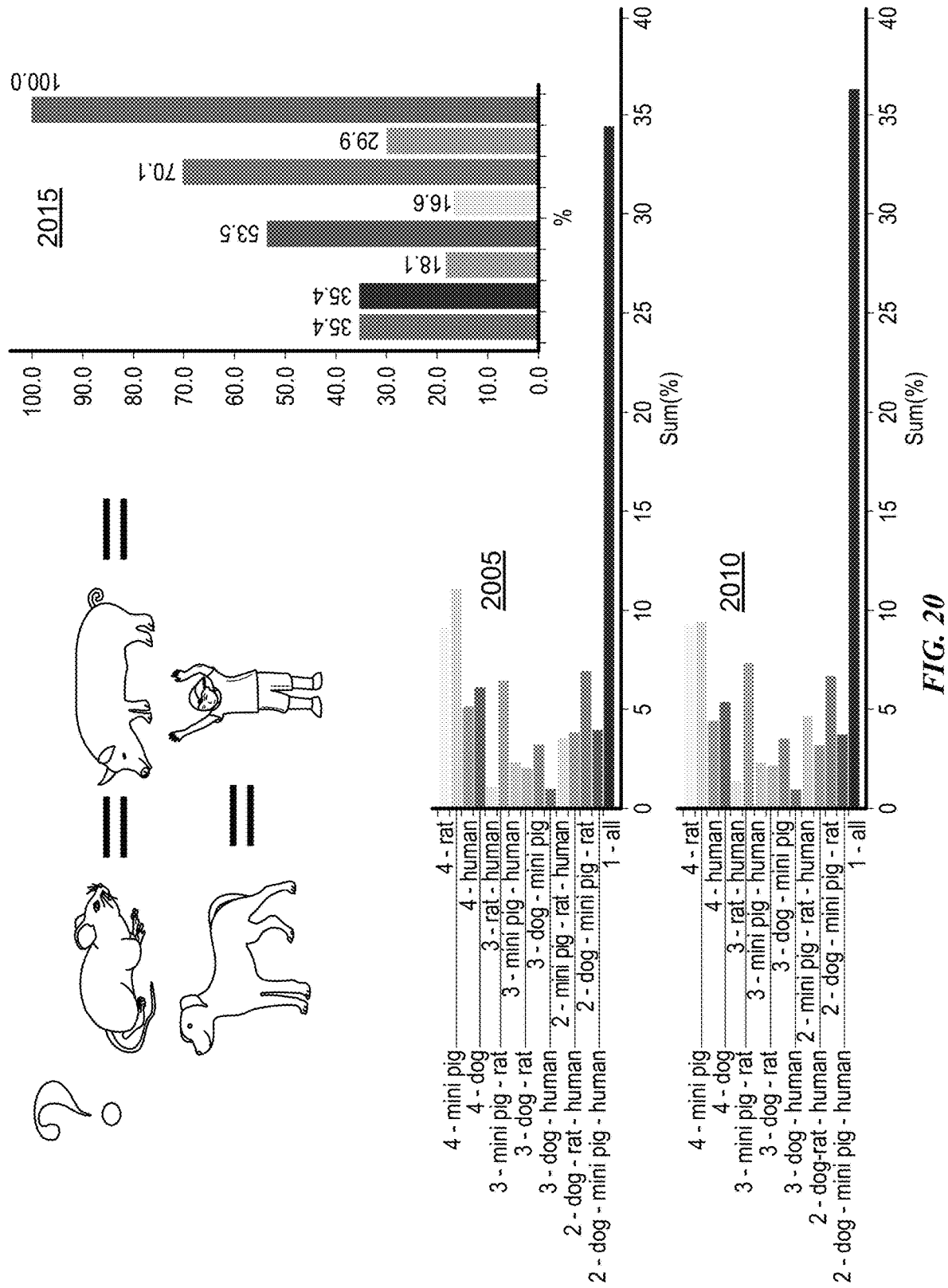

FIG. 18 depicts relative search specificity for a number of parameter combinations normalized to the number of library entries (for instance, incorrectness measure). In the bar graph of FIG. 18, red is for a non-linear gradient and blue is for a linear gradient. FIG. 19 depicts results for various experimental cases, such as panel 1305 depicting compounds detected in all replicates, panel 1910 depicting compounds detected in all human replicates but not consistently in the other species (gradient: light blue=high abundant–dark blue (low abundant)), panel 1915 depicts compounds detected in all dog/rat replicates and sparsely in the other species, and panel 1920 depicts an unsupervised principle component analysis (PCA) for multi-species matrix samples. FIG. 20 depicts relative replication matrix compounds for the 2005 non-linear gradient experiments, 2010 linear gradient experiments, and 2015 the relative and cumulative relative library increase with aggregation on frequency replication.

The experiment A data were also co-detected and the compounds identified in all replicate runs/species retained. As shown in FIG. 19, certain compounds are consistently expressed by all species (for instance, 1905), in other cases detection was more sparse (for instance, 1910), and cases were compounds were strongly expressed in certain species but not others (for instance, 1910). FIG. 20 demonstrates the relative increase in library size by considering co-detection across replicates from multiple species, for example, providing a 47% (mini pig)-99% (human) detection coverage increase.

Figure 21:
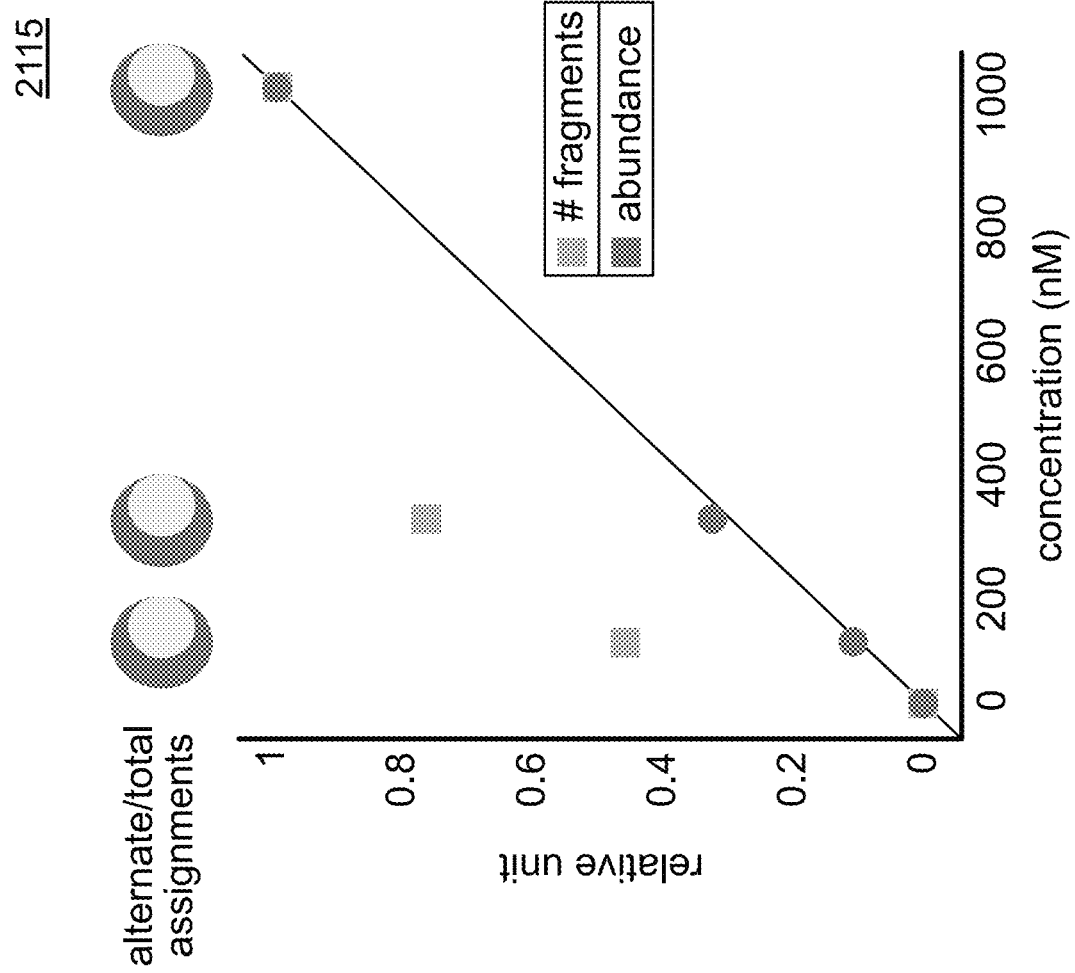
Figure 21:
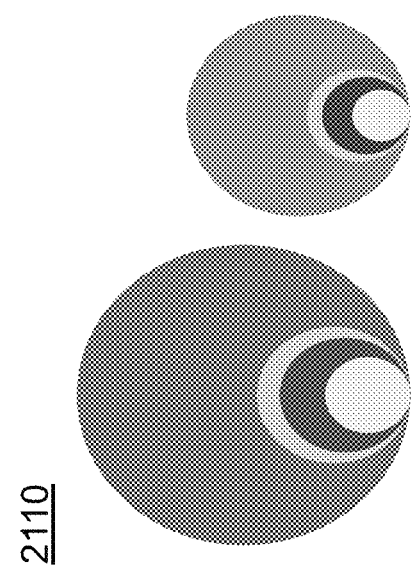

FIG. 21 depicts experiment (B) results, showing the identification of a metabolite of interest in panel 2105, based on m/z, t(r), CCS, and MS/MS using a consensus library including both expected chemical structures (panel 2115) and known-unidentified structures. FIG. 21 also depicts relative FDR value gains in panel 2110, for example, estimated by contrasting a number of components detected inside the specified tolerance windows for any given combination of parameters using the metabolite cocktail compounds as targets, which were all confidently detected at all spike levels.

Figure 22:
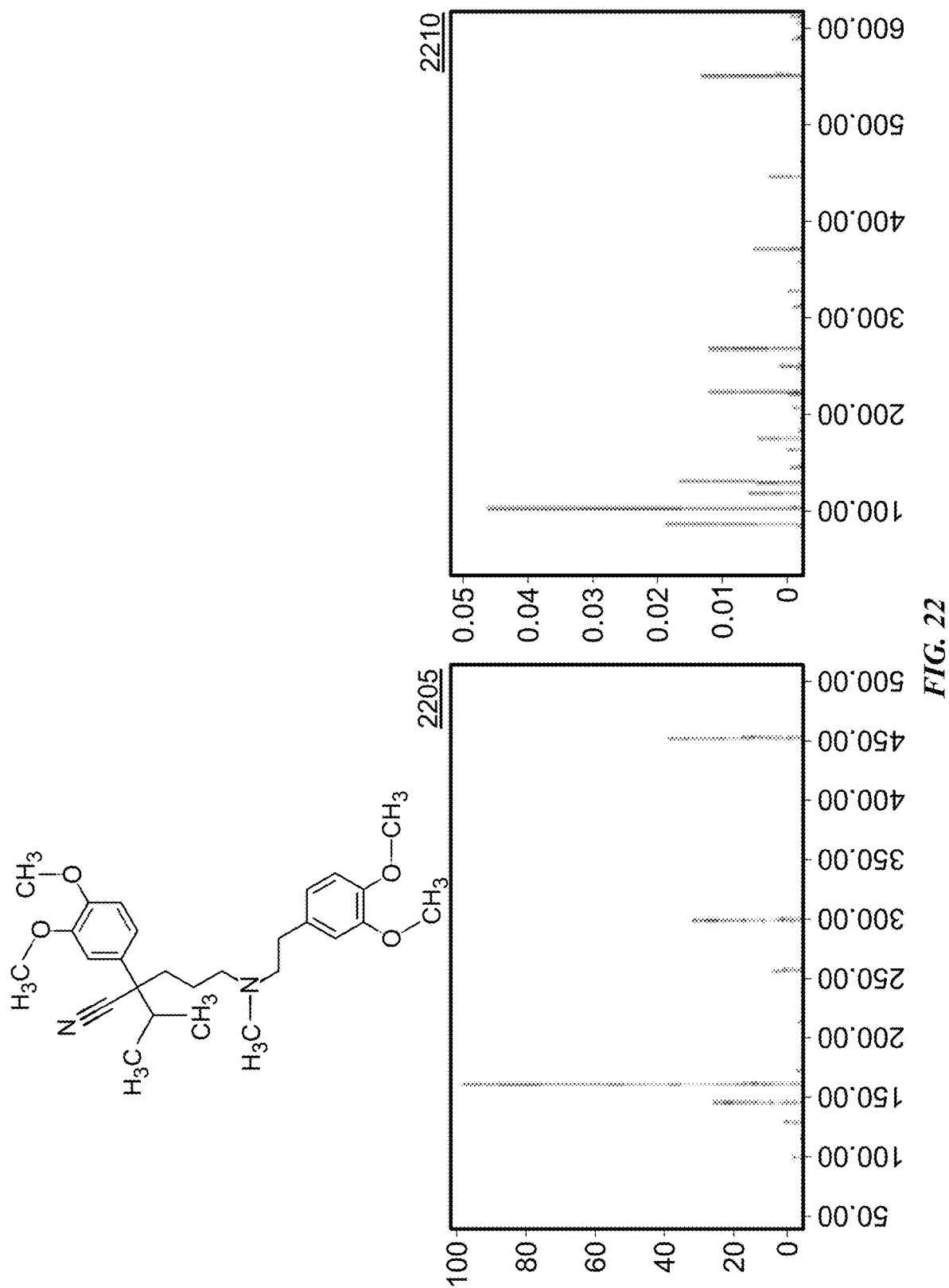
Figure 23:
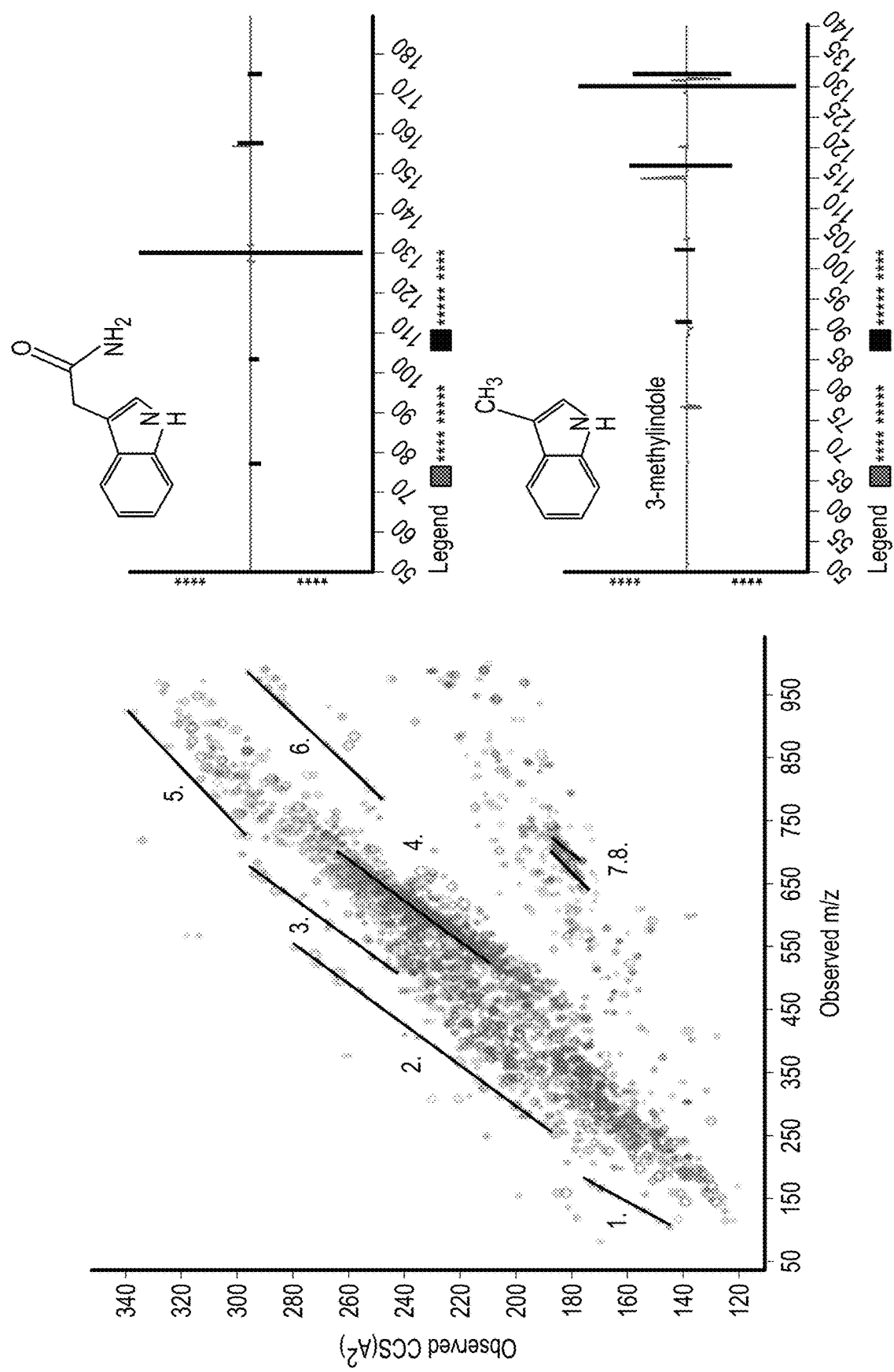
Figure 24:
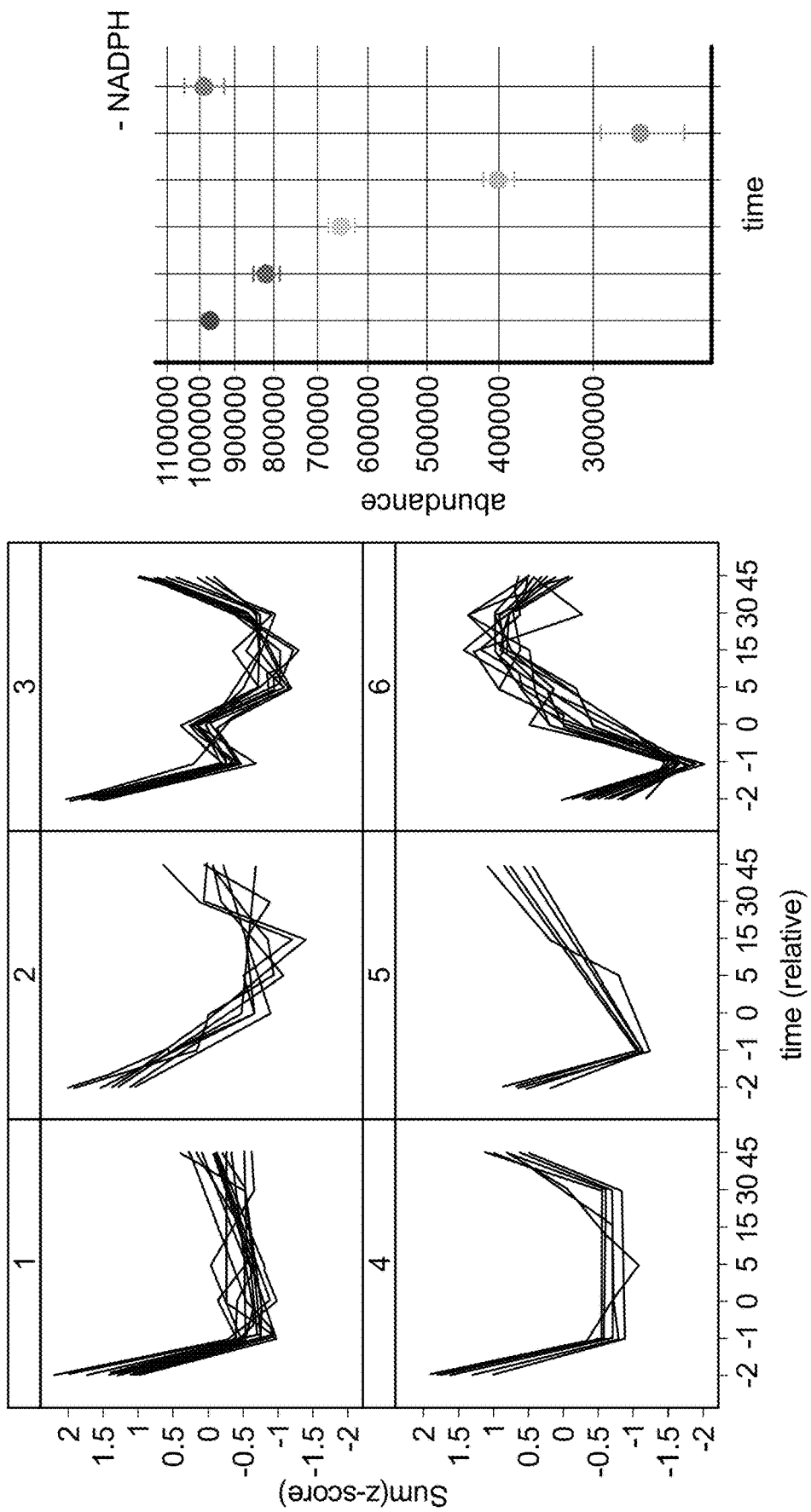

FIG. 22 depicts example consensus spectra of known-identified (or "known-known") (parent drug) in panel 2205 and known-unidentified ("known-unknown") (matrix compound). FIG. 23 depicts an example of class-specific known-unidentified CCS vs. m/z matrix distributions, with, shown in inset, tentative Metlin database identifications from two retention and drift time aligned spectra from one of the class specific trend lines (red=non-linear gradient; blue=linear gradient). FIG. 24 depicts known-unidentified z-score normalized drug-dose induced response profiles (K-means clustering) of known-unidentified human microsomes, with, shown in the inset, the aggregated response (abundance) of three technical replicates of one of the parent drugs in the presence of human microsomal matrix. In general, FIGS. 22-24, summarizing experiment (C), depict potential applications of a consensus library according to some embodiments. For example, aggregated spectra, of FIG. 22, can be utilized for various analytical purposes, such as compound database searching (for instance, FIG. 23), providing context and knowledge to known-unidentified library entries, and/or the like. The response, as well as that of the dosed compounds and its expected metabolites can be readily monitored (for instance, FIG. 24).

Accordingly, Experiment II demonstrates consensus library creation and use, such as a multi-species hepatocyte and microsome known-unidentified consensus libraries that were successfully created, validated, and applied in drug metabolism applications. In addition, CCS and retention time may both contribute to the identification correctness with CCS illustrating reduced matrix effect dependency. Furthermore, the application of MS2 retention and drift time aligned known-unidentified spectra and libraries provides detection, identification, and FDR reduction of both unknowns and (expected) known analytes. In another example, Experiment II demonstrates the conceptual use of multi-species matrix libraries for FDR estimation and the use of multi-species matrix known-unidentified matrix libraries provides for improved drug metabolism analysis efficiency.

Figure 25:
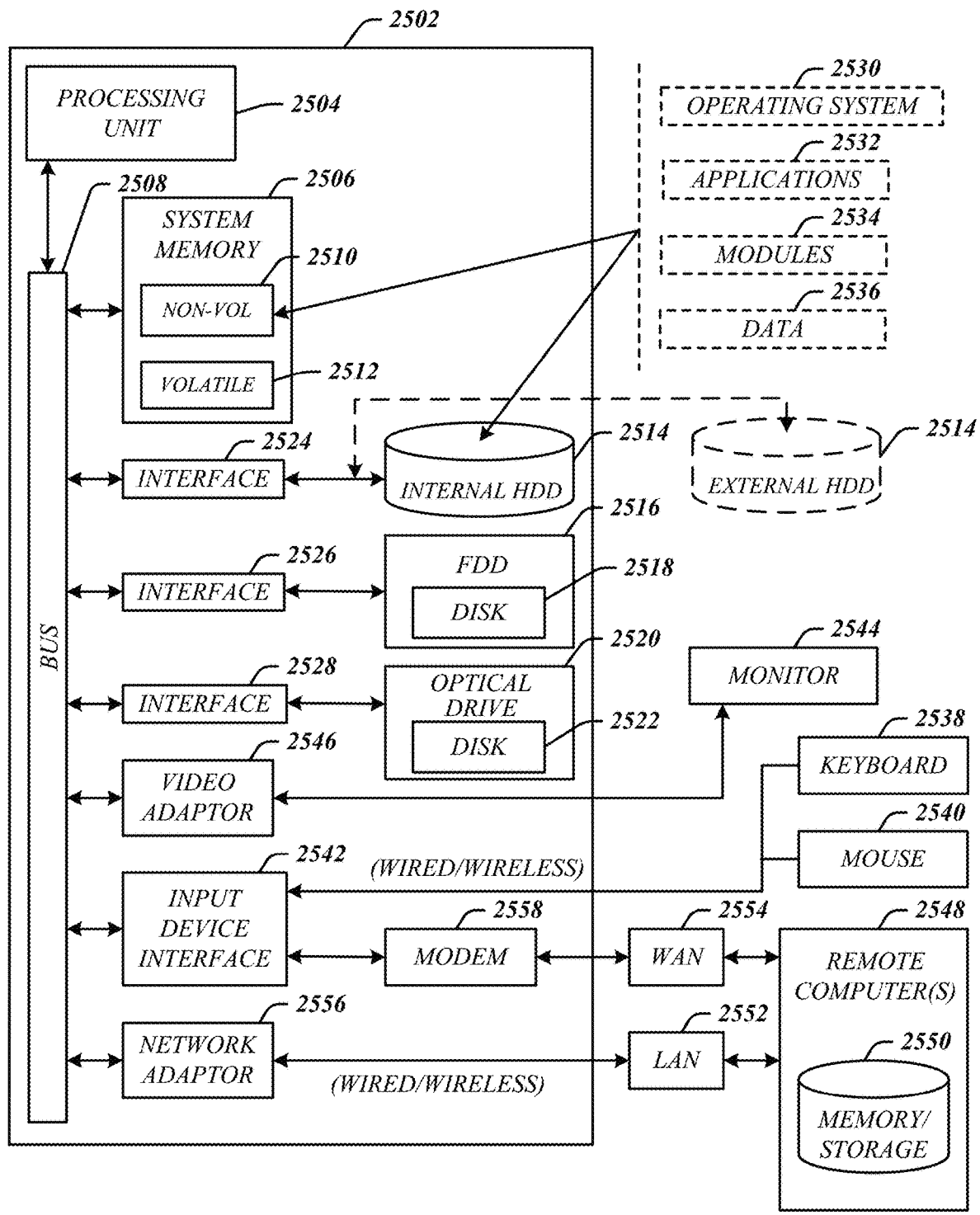
FIG. 25 illustrates an embodiment of a computing architecture.

FIG. 25 illustrates an embodiment of an exemplary computing architecture 1900 suitable for implementing various embodiments as previously described. In various embodiments, the computing architecture 1900 may comprise or be implemented as part of an electronic device. In some embodiments, the computing architecture 1900 may be representative, for example, of apparatus 205, 305, and/or 405. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 1900. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1900 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1900.

As shown in FIG. 19, the computing architecture 1900 comprises a processing unit 1904, a system memory 1906 and a system bus 19019. The processing unit 1904 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 1904.

The system bus 19019 provides an interface for system components including, but not limited to, the system memory 1906 to the processing unit 1904. The system bus 19019 can be any of several types of bus structure that may further interconnect to a memory bus (with or without a memory controller), a peripheral bus, and a local bus using any of a variety of commercially available bus architectures. Interface adapters may connect to the system bus 19019 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 1906 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 19, the system memory 1906 can include non-volatile memory 1910 and/or volatile memory 1912. A basic input/output system (BIOS) can be stored in the non-volatile memory 1910.

The computer 1902 may include various types of computer-readable storage media in the form of one or more lower speed memory units, including an internal (or external) hard disk drive (HDD) 1914, a magnetic floppy disk drive (FDD) 1916 to read from or write to a removable magnetic disk 1919, and an optical disk drive 1920 to read from or write to a removable optical disk 1922 (e.g., a CD-ROM or DVD). The HDD 1914, FDD 1916 and optical disk drive 1920 can be connected to the system bus 19019 by a HDD interface 1924, an FDD interface 1926 and an optical drive interface 1920, respectively. The HDD interface 1924 for external drive implementations can include at least one or both of Universal Serial Bus (USB) and IEEE 1374 interface technologies.

The drives and associated computer-readable media provide volatile and/or nonvolatile storage of data, data structures, computer-executable instructions, and so forth. For example, a number of program modules can be stored in the drives and memory units 1910, 1912, including an operating system 1930, one or more application programs 1932, other program modules 1934, and program data 1936. In one embodiment, the one or more application programs 1932, other program modules 1934, and program data 1936 can include, for example, the various applications and/or components according to some embodiments A user can enter commands and information into the computer 1902 through one or more wire/wireless input devices, for example, a keyboard 1938 and a pointing device, such as a mouse 1940. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1904 through an input device interface 1942 that is coupled to the system bus 1908, but can be connected by other interfaces such as a parallel port, IEEE 1394 serial port, a game port, a USB port, an IR interface, and so forth.

A monitor 1944 or other type of display device is also connected to the system bus 19019 via an interface, such as a video adaptor 1946. The monitor 1944 may be internal or external to the computer 1902. In addition to the monitor 1944, a computer typically includes other peripheral output devices, such as speakers, printers, and so forth.

The computer 1902 may operate in a networked environment using logical connections via wire and/or wireless communications to one or more remote computers, such as a remote computer 19419. The remote computer 1902 can be a workstation, a server computer, a router, a personal computer, portable computer, microprocessor-based entertainment appliance, a peer device or other common network node, and typically includes many or all of the elements described relative to the computer 1902, although, for purposes of brevity, only a memory/storage device 1950 is illustrated. The logical connections depicted include wire/wireless connectivity to a local area network (LAN) 1952 and/or larger networks, for example, a wide area network (WAN) 1954. Such LAN and WAN networking environments are commonplace in offices and companies, and facilitate enterprise-wide computer networks, such as intranets, all of which may connect to a global communications network, for example, the Internet.

When used in a LAN networking environment, the computer 1902 is connected to the LAN 1952 through a wire and/or wireless communication network interface or adaptor 1956. The adaptor 1956 can facilitate wire and/or wireless communications to the LAN 1952, which may also include a wireless access point disposed thereon for communicating with the wireless functionality of the adaptor 1956.

When used in a WAN networking environment, the computer 1902 can include a modem 19519, or is connected to a communications server on the WAN 1954, or has other means for establishing communications over the WAN 1954, such as by way of the Internet. The modem 19519, which can be internal or external and a wire and/or wireless device, connects to the system bus 19019 via the input device interface 1942. In a networked environment, program modules depicted relative to the computer 1902, or portions thereof, can be stored in the remote memory/storage device 1950. It will be appreciated that the network connections shown are exemplary and other means of establishing a communications link between the computers can be used.

The computer 1902 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.\

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. An apparatus, comprising:
   at least one memory; and
   logic coupled to the at least one memory, the logic to:
      receive a plurality of sample matrix data sets for a sample matrix generated via mass analysis of the sample matrix, and
      generate a consensus library for the sample matrix based on the plurality of sample matrix data sets, the consensus library comprising a plurality of known-unidentified components for the sample matrix, the known-unidentified components being components which have an indeterminate structure, but which are known to be from the sample matrix across a variety of conditions.

2. The apparatus of claim 1, the mass analysis performed by at least one analytical instrument comprising at least one of a liquid chromatography (LC) system, a mass spectrometer (MS) system, an ion mobility spectrometer (IMS) system, a high-performance liquid chromatography (HPLC) system, an ultra-performance liquid chromatography (UPLC) system, an ultra-high performance liquid chromatography (UHPLC) system, or a liquid chromatography (LC)-ion mobility spectrometer (IMS)-mass spectrometer (MS) system.

3. The apparatus of claim 1, the sample matrix comprising one of a biological matrix, an environmental matrix, or a chemical matrix.

4. The apparatus of claim 1, the plurality of sample matrix data sets comprising mass-to-charge ratio (m/z), retention time, and collision-cross section (CCS) information.

5. The apparatus of claim 1, the consensus library comprising known-identified components of the sample matrix.

6. The apparatus of claim 1, at least a portion of the plurality of known-unidentified components comprising native components of the sample matrix with an unidentified structure.

7. The apparatus of claim 1, the consensus library comprising an incidence rate for each of the plurality of known-unidentified components.

8. The apparatus of claim 1, the consensus library comprising component characteristics for at least a portion of the plurality of unknown-identified components, the component characteristics comprising at least one of mass-to-charge (m/z) ratio, retention time, collision-cross section (CCS) information, and fragment or fragment ion information.

9. The apparatus of claim 1, the logic to include a known-unidentified component in the plurality of known-unidentified components of the consensus library responsive to the known-unidentified component having a component characteristic over a threshold value, the threshold value comprising at least one of a minimum concentration or a minimum incidence rate.

10. The apparatus of claim 1, the logic to:
receive a sample analysis data set generated via mass analysis of a sample associated with the sample matrix, and
generate an unknown-unidentified data set for the sample via comparing the sample analysis data set with a consensus library for the sample matrix.

11. The apparatus of claim 10, the comparison based on mass-to-charge ratio (m/z) collision-cross section (CCS), retention time, and tandem mass spectrometry (MS/MS) information of the sample analysis data set.

12. A computer-implemented method, comprising, by a processor of a computing device:
receiving a plurality of sample matrix data sets for a sample matrix generated via mass analysis of the sample matrix; and
generating a consensus library for the sample matrix based on the plurality of sample matrix data sets, the consensus library comprising a plurality of known-unidentified components for the sample matrix, the known-unidentified components being components which have an indeterminate structure, but which are known to be from the sample matrix across a variety of conditions.

13. The computer-implemented method of claim 12, the mass analysis performed by at least one analytical instrument comprising at least one of a liquid chromatography (LC) system, a mass spectrometer (MS) system, an ion mobility spectrometer (IMS) system, a high-performance liquid chromatography (HPLC) system, an ultra-performance liquid chromatography (UPLC) system, an ultra-high performance liquid chromatography (UHPLC) system or a liquid chromatography (LC)-ion mobility spectrometer (IMS)-mass spectrometer (MS) system.

14. The computer-implemented method of claim 12, the plurality of sample matrix data sets comprising mass-to-charge ratio (m/z), retention time, and collision-cross section (CCS) information.

15. The computer-implemented method of claim 12, the consensus library comprising known-identified components of the sample matrix.

16. The computer-implemented method of claim 12, at least a portion of the plurality of known-unidentified components comprising native components of the sample matrix with an unidentified structure.

17. The computer-implemented method of claim 12, the consensus library comprising at least one of:
an incidence rate for each of the plurality of known-unidentified components, or component characteristics for at least a portion of the plurality of known-unidentified components, the component characteristics comprising at least one of mass-to-charge (m/z) ratio, retention time, collision-cross section (CCS) information, and fragmentation or fragment ion information.

18. The computer-implemented method of claim 12, comprising including a known-unidentified component in the plurality of known-unidentified components of the consensus library responsive to the known-unidentified component having a component characteristic over a threshold value comprising at least one of a minimum concentration or a minimum incidence rate.

19. The computer-implemented method of claim 12, comprising:
receiving a sample analysis data set generated via mass analysis of a sample associated with the sample matrix; and
generating an unknown-unidentified data set for the sample via comparing the sample analysis data set with a consensus library for the sample matrix.

20. The computer-implemented method of claim 12, the comparison based on mass-to-charge ratio (m/z) collision cross section (CCS), retention time, and tandem mass spectrometry (MS/MS) information of the sample analysis data set.

* * * * *